United States Patent
Jones et al.

(10) Patent No.: US 12,084,502 B2
(45) Date of Patent: Sep. 10, 2024

(54) CD33-BINDING POLYPEPTIDES AND USES THEREOF

(71) Applicant: Inhibrx Biosciences, Inc., La Jolla, CA (US)

(72) Inventors: Kyle S. Jones, San Marcos, CA (US); William Crago, San Diego, CA (US); Angelica Sanabria, La Jolla, CA (US); Andrew Hollands, La Jolla, CA (US); Jacob Gano, Encinitas, CA (US); Milton Ma, La Jolla, CA (US); John C. Timmer, San Diego, CA (US); Brendan P. Eckelman, Encinitas, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 14 days.

(21) Appl. No.: 18/067,504

(22) Filed: Dec. 16, 2022

(65) Prior Publication Data
US 2023/0312716 A1   Oct. 5, 2023

Related U.S. Application Data

(62) Division of application No. 16/864,480, filed on May 1, 2020, now Pat. No. 11,560,428.

(60) Provisional application No. 62/844,359, filed on May 7, 2019, provisional application No. 62/843,408, filed on May 4, 2019.

(51) Int. Cl.
*C07K 16/28*   (2006.01)
*A61K 45/06*   (2006.01)
*A61K 47/55*   (2017.01)

(52) U.S. Cl.
CPC .......... *C07K 16/2809* (2013.01); *A61K 47/55* (2017.08); *C07K 16/2818* (2013.01); *C07K 16/283* (2013.01); *C07K 16/2851* (2013.01); *A61K 45/06* (2013.01); *C07K 2317/24* (2013.01); *C07K 2317/31* (2013.01); *C07K 2317/52* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 2010/0003253 | A1 | 1/2010 | Laeremans et al. |
| 2016/0096892 | A1 | 4/2016 | Brogdon et al. |
| 2016/0311901 | A1 | 10/2016 | Jarjour et al. |
| 2018/0237533 | A1 | 8/2018 | Cellectis |

FOREIGN PATENT DOCUMENTS

| | | |
|---|---|---|
| WO | 2015017214 A1 | 2/2015 |
| WO | 2015089344 A1 | 6/2015 |
| WO | 2015142661 A1 | 9/2015 |
| WO | 2016014576 A1 | 1/2016 |
| WO | 2017025038 A1 | 2/2017 |
| WO | 2018175988 A1 | 9/2018 |
| WO | 2019006280 A1 | 1/2019 |

OTHER PUBLICATIONS

De Pascaslis et al. "Grafting of abbreviated complementarity determining regions containing specificity determining residues essential for ligand contact to engineer a less immunogenic humanzied monoclonal antibody", Journal of Immunology, vol. 169, pp. 3076-3084 (2002).
Goel et al. Plasticity within the Antigen-Combining Site May Manifest as Molecular Mimicry in the Humoral Immune Response.1 J. Immunol. 173(12), pp. 7358-7367 (2004).
International Search Report and Written Opinion for International Application No. PCT/US2020/030969 dated Oct. 20, 2020, 18 pages.
International Search Report and Written Opinion for International Application No. PCT/US2020/31780 dated Oct. 1, 2020, 12 pages.
Invitation to Pay Fees for International Application No. PCT/US2020/031780 dated Aug. 14, 2020, 3 pages.
Kahn et al. 'Adjustable Locks and Flexible Keys: Plasticity of Epitope-Paratope Interactions in Germline Antibodies.' J. Immunol. 192, pp. 5398-5405 (2014).
Maccallum et al. "Antibody-antigen interactions: contact analysis and binding site topography", Journal of Molecular Biology, vol. 262, pp. 732-745 (1996).
Muyldermans, S., "Nanobodies: Natural Single-Domain Antibodies," Annual Review of Biochemistry (82)(1), pp. 775-797 (2013).
Poosarla et al. 'Computational De Novo Design of Antibodies Binding to a Peptide With High Affinity.' Biotech. Bioeng. 114(6): 1331-1342 (2017).
Vincke et al., "Generation of Single Domain Antibody Fragments Derived from Camelids and Generation of Manifold Constructs Ed," Methods in Molecular Biology, Humana PR, US, vol. 907, pp. 145-176 (2012).
33rd Annual Meeting & Pre-Conference Programs of the Society for Immunotherapy of Cancer (SITC 2018); Journal for Immunotherapy of Cancer 2018, 6(Suppl 1):114; P270 (pp. 138-139).
Minagawa et al., "In Vitro Pre-Clinical Validation of Suicide Gene Modified Anti-CD33 Redirected Chimeric Antigen Receptor T-Cells for Acute Myeloid Leukemia," PLOS One, pp. 1-25 (2016).

*Primary Examiner* — Nora M Rooney
(74) *Attorney, Agent, or Firm* — McNeill PLLC

(57) ABSTRACT

Provided herein are VHH-containing polypeptides that bind CD33. Uses of the VHH-containing polypeptides are also provided.

27 Claims, 8 Drawing Sheets
Specification includes a Sequence Listing.

CD33-BINDING POLYPEPTIDES AND USES THEREOF

CROSS-REFERENCE TO RELATED APPLICATIONS

This application is a divisional of U.S. application Ser. No. 16/864,480, filed May 1, 2020, which claims the benefit of priority of U.S. Provisional Application No. 62/843,408, filed May 4, 2019, and U.S. Provisional Application No. 62/844,359, filed May 7, 2019, each of which is incorporated by reference herein in its entirety for any purpose.

SEQUENCE LISTING

The present application contains a Sequence Listing which has been submitted electronically in XML format and is hereby incorporated by reference in its entirety. Said XML copy, created on Dec. 16, 2022, is named "2022-12-16_01202-0022-01US_ST26.xml" and is 176,314 bytes in size. The information in the electronic format of the sequence listing is incorporated herein by reference in its entirety.

FIELD

The present invention relates to CD33-binding polypeptides, and methods of using CD33-binding polypeptides to modulate the biological activity of CD33. Such methods include, but are not limited to, methods of treating cancer.

BACKGROUND

CD33, also known as p67, SIGLEC3, or SIGLEC-3, binds sialic acids and regulates inflammatory and immune responses of hematopoietic cells. CD33 also can influence initiation, proliferation and progression in a variety of hematologic cancers. For example, over 85% of acute myeloid leukemia (AML) cases express the CD33 antigen. Thus, CD33 is a suitable tumor-associated antigen for targeted therapies for hematologic cancers, such as leukemia. Therefore, there exists a therapeutic need for more potent antagonists of CD33.

SUMMARY

Provided herein are CD33-binding polypeptides and methods of using CD33-binding polypeptides to treat, for example, leukemia. In some embodiments, a CD33-binding polypeptide comprises at least one VHH domain. Some embodiments are provided below.

Embodiment 1. A polypeptide comprising at least one VHH domain that binds CD33 and that comprises a CDR1 comprising the amino acid sequence of SEQ ID NO: 47, 3, 7, 11, 15, 19, 23, 27, 31, 35, 50, 53, 56, 59, 62, 65, 68, or 71; a CDR2 comprising the amino acid sequence of SEQ ID NO: 48, 4, 8, 12, 16, 20, 24, 28, 32, 36, 51, 54, 57, 60, 63, 66, 69, or 72; and a CDR3 comprising the amino acid sequence of SEQ ID NO: 49, 5, 9, 13, 17, 21, 25, 29, 33, 37, 52, 55, 58, 61, 64, 67, 70, or 73.

Embodiment 2. The polypeptide of embodiment 1, wherein at least one VHH domain comprises a CDR1 comprising the amino acid sequence of SEQ ID NO: 47 or 3; a CDR2 comprising the amino acid sequence of SEQ ID NO: 48 or 4; and a CDR3 comprising the amino acid sequence of SEQ ID NO: 49 or 5.

Embodiment 3. The polypeptide of embodiment 1 or embodiment 2, wherein at least one VHH domain comprises a CDR1 comprising the amino acid sequence of SEQ ID NO: 7; a CDR2 comprising the amino acid sequence of SEQ ID NO: 8; and a CDR3 comprising the amino acid sequence of SEQ ID NO: 9.

Embodiment 4. The polypeptide of any one of embodiments 1-3, wherein at least one VHH domain comprises a CDR1 comprising the amino acid sequence of SEQ ID NO: 11 or 50; a CDR2 comprising the amino acid sequence of SEQ ID NO: 12 or 51; and a CDR3 comprising the amino acid sequence of SEQ ID NO: 13 or 52.

Embodiment 5. The polypeptide of any one of embodiments 1-4, wherein at least one VHH domain comprises a CDR1 comprising the amino acid sequence of SEQ ID NO: 15, 53, or 56; a CDR2 comprising the amino acid sequence of SEQ ID NO: 16, 54, or 57; and a CDR3 comprising the amino acid sequence of SEQ ID NO: 17, 55, or 58.

Embodiment 6. The polypeptide of any one of embodiments 1-5, wherein at least one VHH domain comprises a CDR1 comprising the amino acid sequence of SEQ ID NO: 19 or 59; a CDR2 comprising the amino acid sequence of SEQ ID NO: 20 or 60; and a CDR3 comprising the amino acid sequence of SEQ ID NO: 21 or 61.

Embodiment 7. The polypeptide of any one of embodiments 1-6, wherein at least one VHH domain comprises a CDR1 comprising the amino acid sequence of SEQ ID NO: 23 or 62; a CDR2 comprising the amino acid sequence of SEQ ID NO: 24 or 63; and a CDR3 comprising the amino acid sequence of SEQ ID NO: 25 or 64.

Embodiment 8. The polypeptide of any one of embodiments 1-7, wherein at least one VHH domain comprises a CDR1 comprising the amino acid sequence of SEQ ID NO: 27 or 65; a CDR2 comprising the amino acid sequence of SEQ ID NO: 28 or 66; and a CDR3 comprising the amino acid sequence of SEQ ID NO: 29 or 67.

Embodiment 9. The polypeptide of any one of embodiments 1-8, wherein at least one VHH domain comprises a CDR1 comprising the amino acid sequence of SEQ ID NO: 31 or 68; a CDR2 comprising the amino acid sequence of SEQ ID NO: 32 or 69; and a CDR3 comprising the amino acid sequence of SEQ ID NO: 33 or 70.

Embodiment 10. The polypeptide of any one of embodiments 1-9, wherein at least one VHH domain comprises a CDR1 comprising the amino acid sequence of SEQ ID NO: 35 or 71; a CDR2 comprising the amino acid sequence of SEQ ID NO: 36 or 72; and a CDR3 comprising the amino acid sequence of SEQ ID NO: 37 or 73.

Embodiment 11. The polypeptide of any one of embodiments 1-10, wherein at least one VHH domain comprises a CDR1, a CDR2, and a CDR3, respectively comprising the amino acid sequences of SEQ ID NOs: 47, 48, and 49; SEQ ID NOs: 3, 4, and 5; SEQ ID NOs: 7, 8, and 9; SEQ ID NOs: 11, 12, and 13; SEQ ID NOs: 15, 16, and 17; SEQ ID NOs: 19, 20, and 21; SEQ ID NOs: 23, 24, and 25; SEQ ID NOs: 27, 28, and 29; SEQ ID NOs: 31, 32, and 33; SEQ ID NOs: 35, 36, and 37; SEQ ID NOs: 50, 51, and 52; SEQ ID NOs: 53, 54, and 55; SEQ ID NOs: 56, 57, and 58; SEQ ID NOs: 59, 60, and 61; SEQ ID NOs: 62, 63, and 64; SEQ ID NOs: 65, 66, and 67; SEQ ID NOs: 68, 69, and 70; or SEQ ID NOs: 71, 72, and 73.

Embodiment 12. The polypeptide of any one of embodiments 1-11, wherein at least one VHH domain is humanized.

Embodiment 13. The polypeptide of any one of embodiments 1-12, wherein at least one VHH domain comprises an amino acid sequence at least 85%, at least 90%, at least 95%, or at least 99% identical to the amino acid sequence of SEQ ID NO: 38, 114, 39, 40, 41, 42, 43, 44, 45, 46, 115, 116, 117, 118, 119, 120, 121, or 122.

Embodiment 14. The polypeptide of any one of embodiments 1-12, wherein at least one VHH domain comprises the amino acid sequence of SEQ ID NO: 38, 114, 39, 40, 41, 42, 43, 44, 45, 46, 115, 116, 117, 118, 119, 120, 121, or 122.

Embodiment 15. The polypeptide of any one of embodiment 1-12, wherein at least one VHH domain comprises an amino acid sequence at least 85%, at least 90%, at least 95%, or at least 99% identical to the amino acid sequence of SEQ ID NO: 2, 6, 10, 14, 18, 22, 26, 30, 34, 123, 124, 125, 126, 127, 128, 129, 130, or 131.

Embodiment 16. The polypeptide of any one of embodiments 1-12, wherein at least one VHH domain comprises the amino acid sequence of SEQ ID NO: 2, 6, 10, 14, 18, 22, 26, 30, 34, 123, 124, 125, 126, 127, 128, 129, 130, or 131.

Embodiment 17. The polypeptide of any one of embodiments 1-16, comprising two VHH domains.

Embodiment 18. The polypeptide of any one of embodiments 1-16, comprising three VHH domains.

Embodiment 19. The polypeptide of any one of embodiments 1-18, wherein the polypeptide comprises at least one binding domain that binds an antigen other than CD33.

Embodiment 20. The polypeptide of embodiment 19, wherein the polypeptide comprises at least one binding domain that binds CD3, T-cell receptor (TCR) α, TCRβ, CD28, CD16, CD32A, CD64, CD89, NKp46, or NKG2D.

Embodiment 21. The polypeptide of embodiment 17 or 18, wherein each VHH domain binds CD33.

Embodiment 22. The polypeptide of embodiment 21, wherein each VHH domain comprises the same CDR1, CDR2, and CDR3 amino acid sequences.

Embodiment 23. The polypeptide of embodiment 21, wherein each VHH domain comprises the same VHH sequence.

Embodiment 24. The polypeptide of any one of embodiments 1-16, comprising one VHH domain.

Embodiment 25. The polypeptide of any one of embodiments 1-24, wherein the polypeptide comprises an Fc region.

Embodiment 26. The polypeptide of embodiment 25, wherein the Fc region comprises an amino acid sequence selected from SEQ ID NOs: 74-109.

Embodiment 27. The polypeptide of embodiment 25 or embodiment 26, which forms a dimer under physiological conditions.

Embodiment 28. The polypeptide of any one of embodiments 1-27, wherein the CD33 is human CD33.

Embodiment 29. The polypeptide of embodiment 28, wherein the human CD33 comprises the sequence of SEQ ID NO: 1.

Embodiment 30. An immunoconjugate comprising the polypeptide of any one of embodiments 1-29 and a cytotoxic agent.

Embodiment 31. The immunoconjugate of embodiment 30, wherein the cytotoxic agent is selected from a calicheamicin, an auristatin, a dolastatin, a tubulicin, a maytansinoid, a cryptophycin, a duocarmycin, an esperamicin, a pyrrolobenzodiazepine, and an enediyne antibiotic.

Embodiment 32. A pharmaceutical composition comprising the polypeptide of any one of embodiments 1-29 or the immunoconjugate of embodiment 30 or embodiment 31, and a pharmaceutically acceptable carrier.

Embodiment 33. An isolated nucleic acid that encodes the polypeptide of any one of embodiments 1-29.

Embodiment 34. A vector comprising the nucleic acid of embodiment 33.

Embodiment 35. A host cell comprising the nucleic acid of embodiment 33 or the vector of embodiment 34.

Embodiment 36. A host cell that expresses the polypeptide of any one of embodiments 1-29.

Embodiment 37. A method of producing the polypeptide of any one of embodiments 1-29, comprising incubating the host cell of embodiment 35 or embodiment 36 under conditions suitable for expression of the polypeptide.

Embodiment 38. The method of embodiment 37, further comprising isolating the polypeptide.

Embodiment 39. A method of treating cancer comprising administering to a subject with cancer a pharmaceutically effective amount of the polypeptide of any one of embodiments 1-29, the immunoconjugate of embodiment 30 or embodiment 31, or the pharmaceutical composition of embodiment 32.

Embodiment 40. The method of embodiment 39, wherein the cancer is selected from lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; chronic lymphocytic leukemia (CLL); acute lymphoblastic leukemia (ALL); acute myeloid leukemia (AML); Hairy cell leukemia; and chronic myeloblastic leukemia.

Embodiment 41. The method of embodiment 39 or 40, wherein the cancer is acute myeloid leukemia (AML).

Embodiment 42. The method of any one of embodiments 39-41, further comprising administering an additional therapeutic agent.

Embodiment 43. The method of embodiment 42, wherein the additional therapeutic agent is an anti-cancer agent.

Embodiment 44. The method of embodiment 43, wherein the anti-cancer agent is selected from a chemotherapeutic agent, an anti-cancer biologic, radiation therapy, CAR-T therapy, and an oncolytic virus.

Embodiment 45. The method of any one of embodiments 39-44, wherein the cancer is a CD33-expressing cancer.

BRIEF DESCRIPTION OF THE FIGURES

FIG. 2A shows binding of 1E4-IgG1 to CD33. FIG. 2B shows binding of hz1E4v2-IgG1 to CD33. FIG. 2C shows binding of 1H9-IgG1 to CD33. FIG. 2D shows binding of hz1H9v2-IgG1 to CD33. FIG. 2E shows binding of hz1G3v3-IgG1 to CD33. FIG. 2F shows binding of 1C7-IgG1 to CD33. FIG. 2G shows binding of hz1C7v1-IgG1 to CD33. FIG. 2H shows binding of hz1C7v11-IgG1 to CD33. FIG. 2I shows binding of hzA07v4-IgG1 to CD33. FIG. 2J shows binding of hzB07v7-IgG1 to CD33. FIG. 2K shows binding of hzG11v2-IgG1 to CD33. FIG. 2L shows binding of F02-IgG1 to CD33. FIG. 2M shows binding of hzF02v18-IgG1 to CD33.

DETAILED DESCRIPTION

Figure 1:
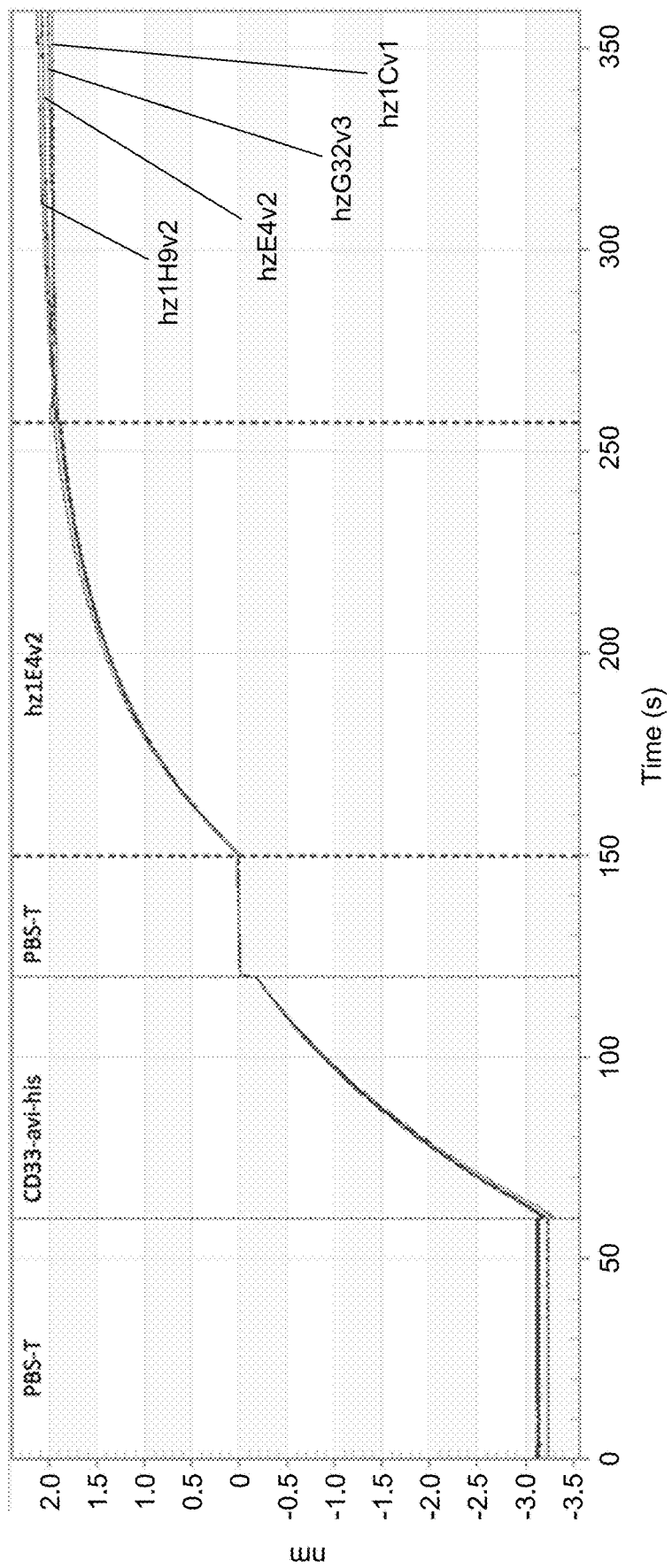
FIG. 1 shows Bio-Layer Interferometry data for hz1E4v2 compared to other CD33-binding sdAbs described herein.
Figure 2A:
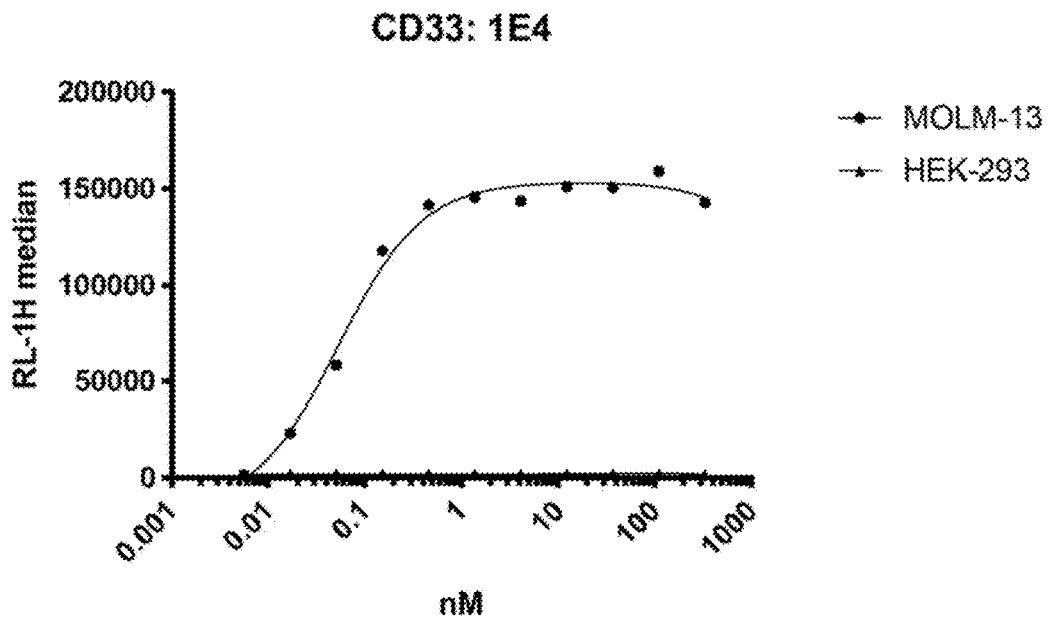
FIG. 2A-2M show binding of certain single-domain antibodies (sdAbs) to CD33 expressed on MOLM-13 or HEK 293 cells. "MOLM-13" indicates MOL-13 cells that have been transfected with a plasmid encoding CD33, as described in Example 2. "CD33m" indicates a truncated CD33 protein (SEQ ID NO: 113). "CD33M" indicates a full length CD33 protein (SEQ ID NO: 112). "HEK 293" or "Parental HEK 293" indicates untransfected HEK 293 cells.
Figure 2B:
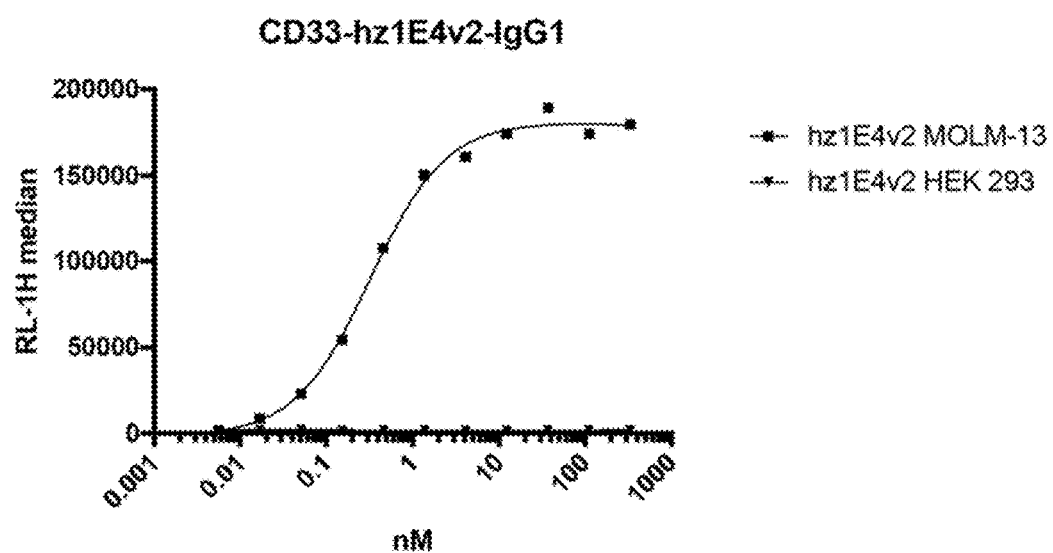
Figure 2C:
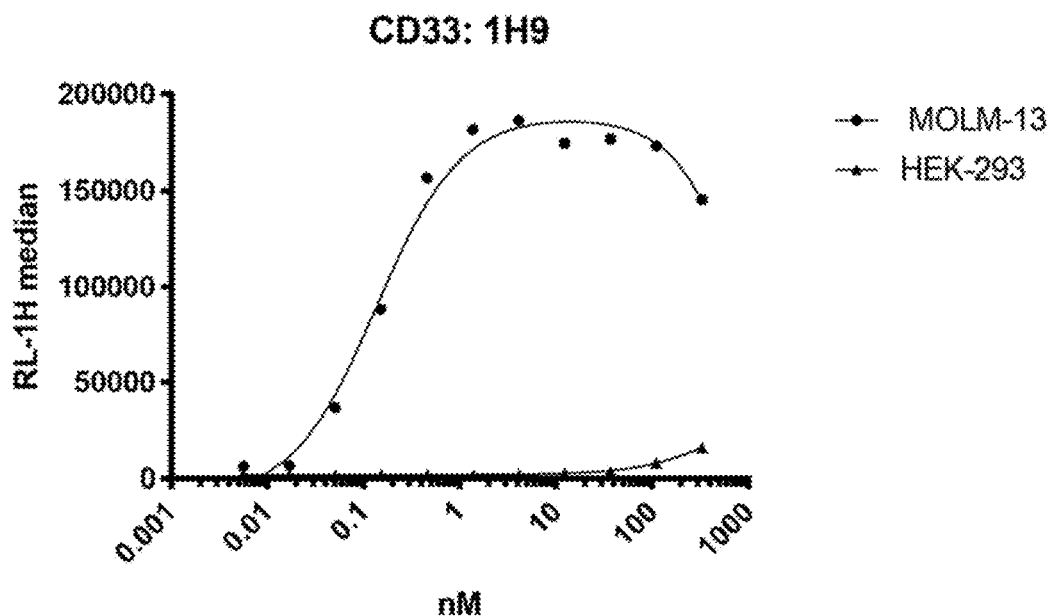
Figure 2D:
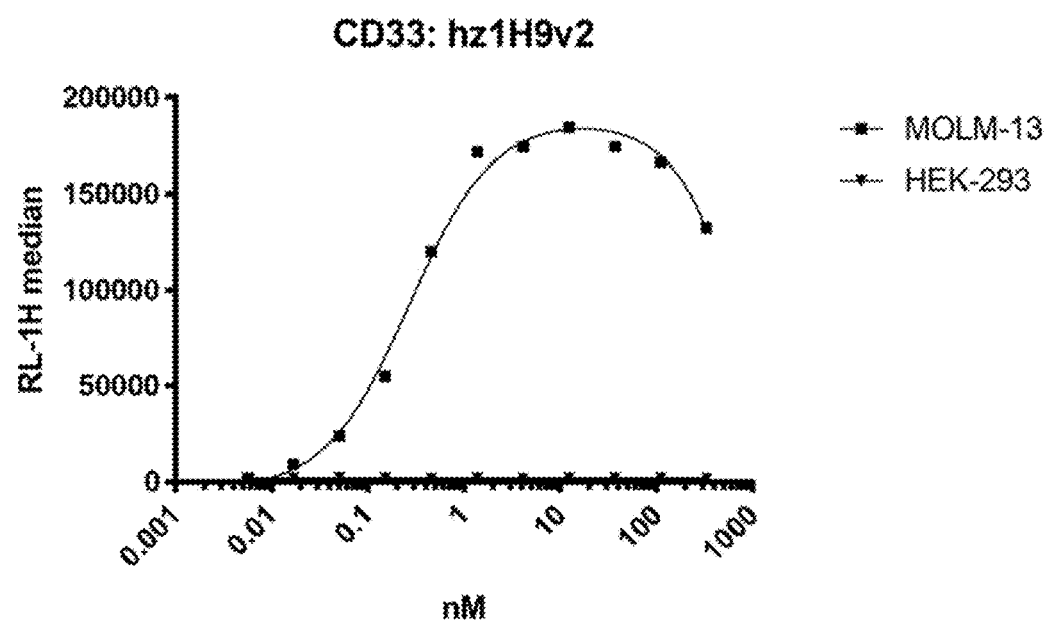
Figure 2E:
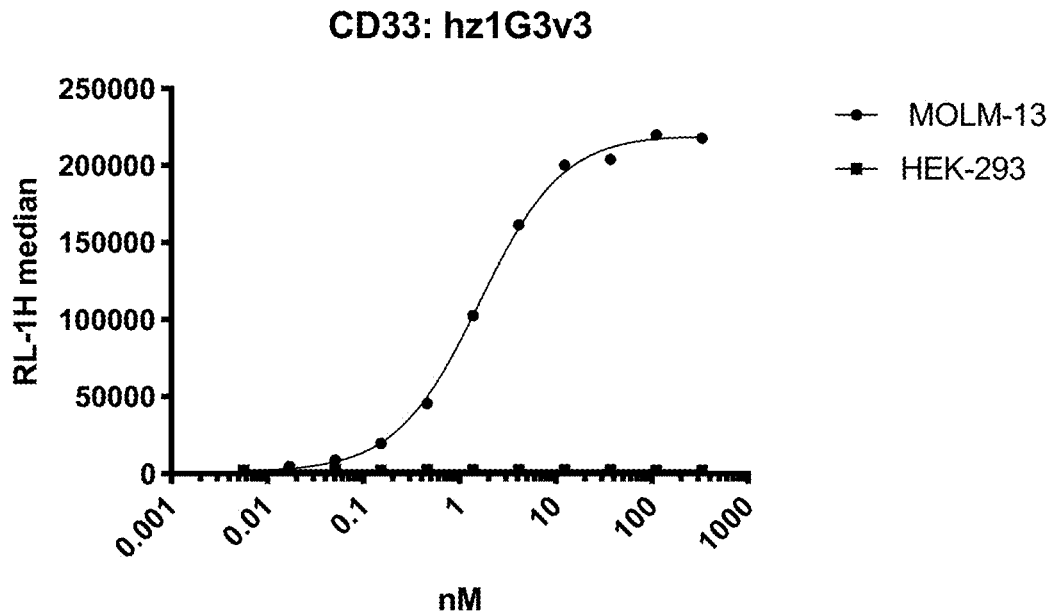
Figure 2F:
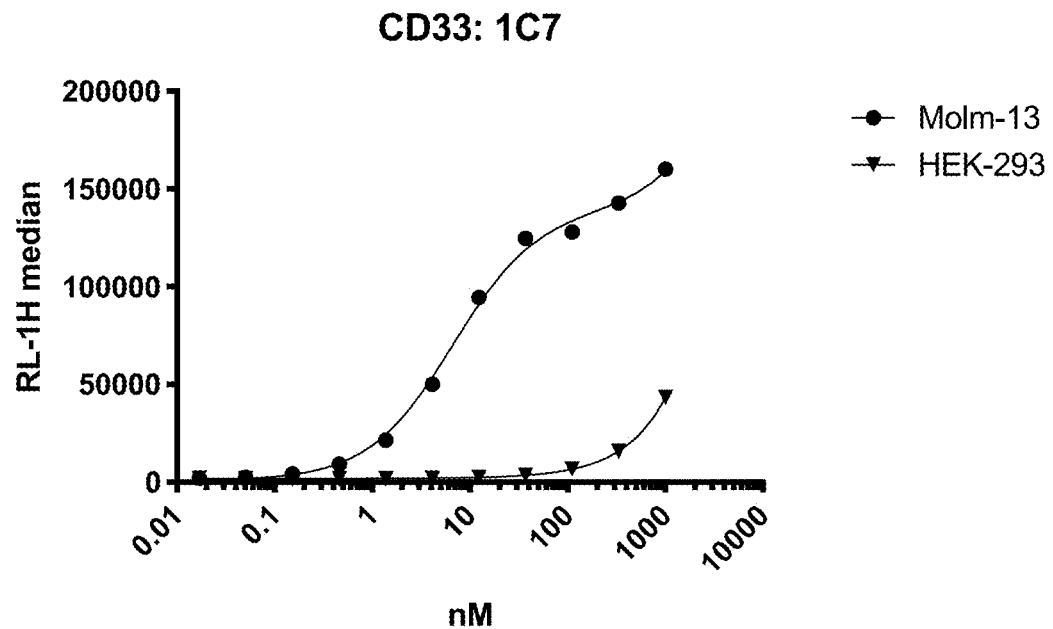
Figure 2G:
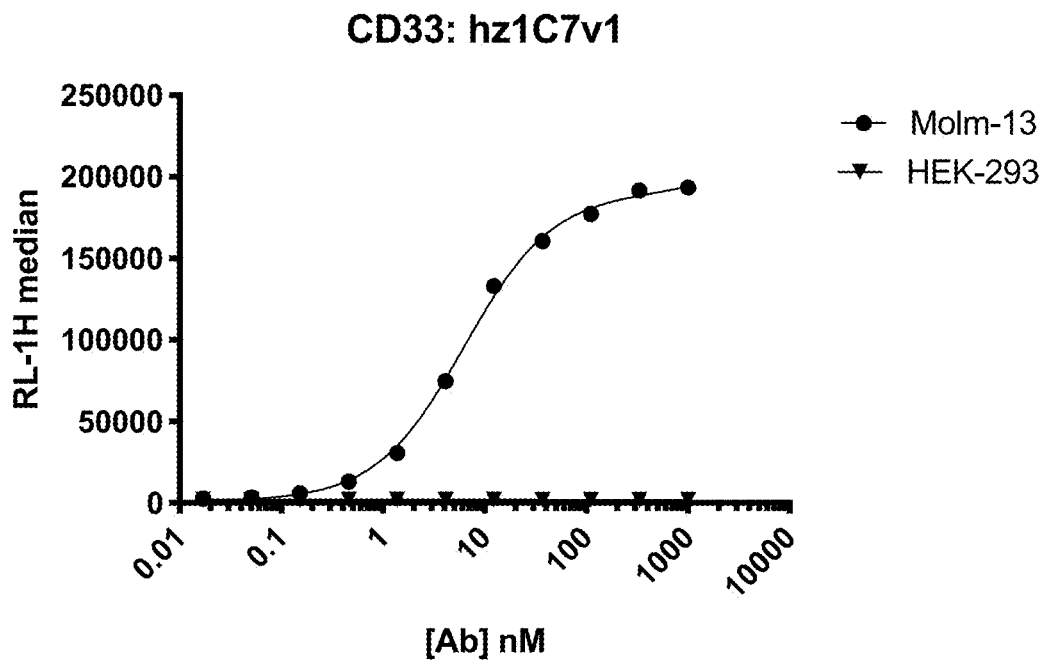
Figure 2H:
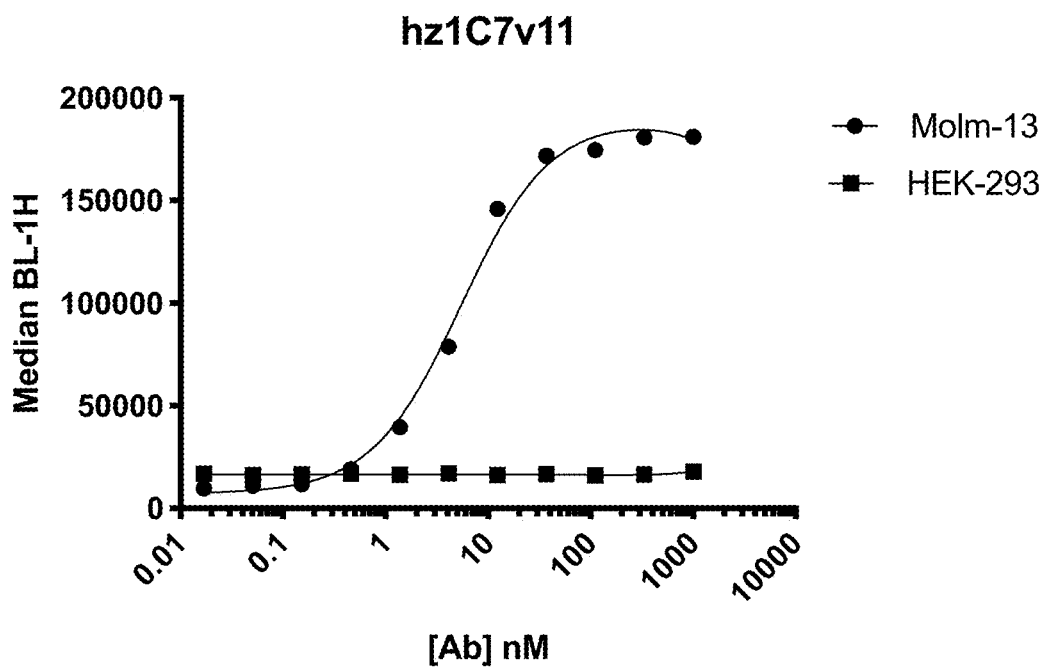
Figure 2I:
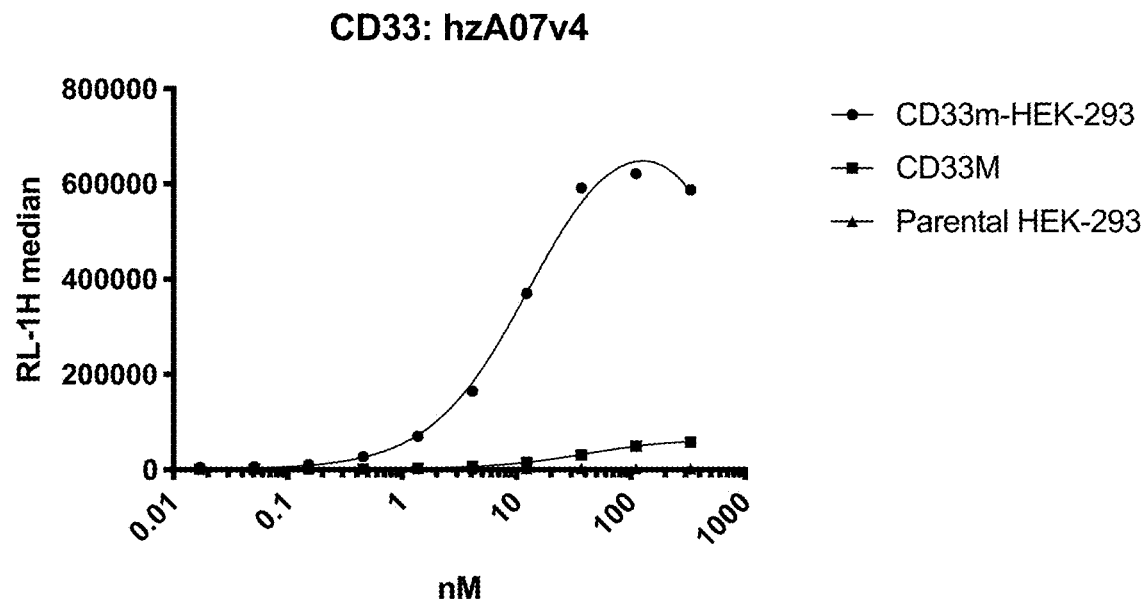
Figure 2J:
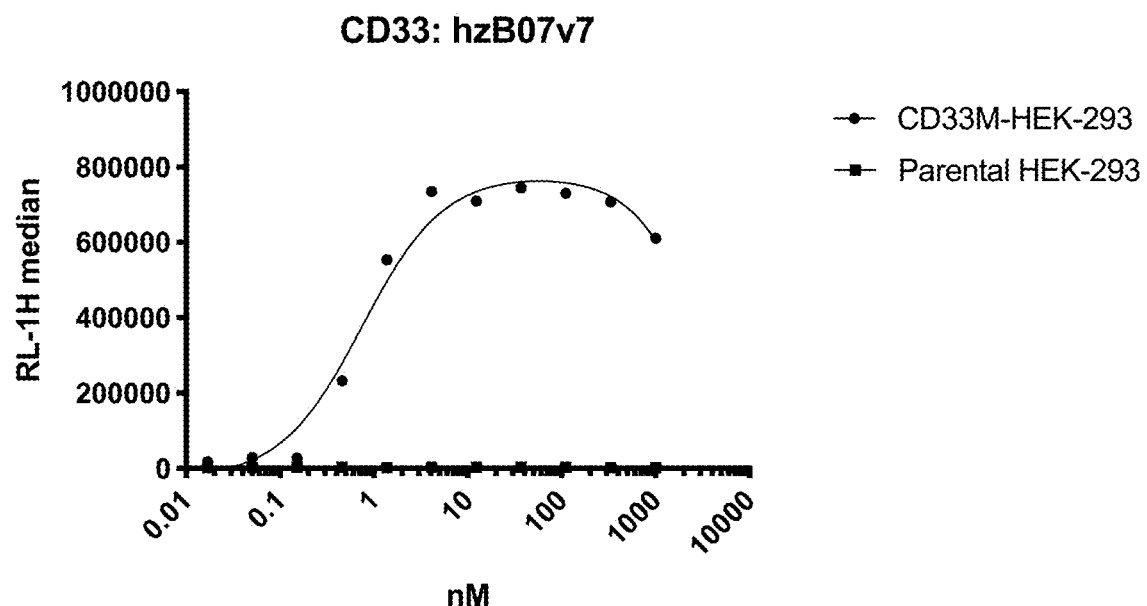
Figure 2K:
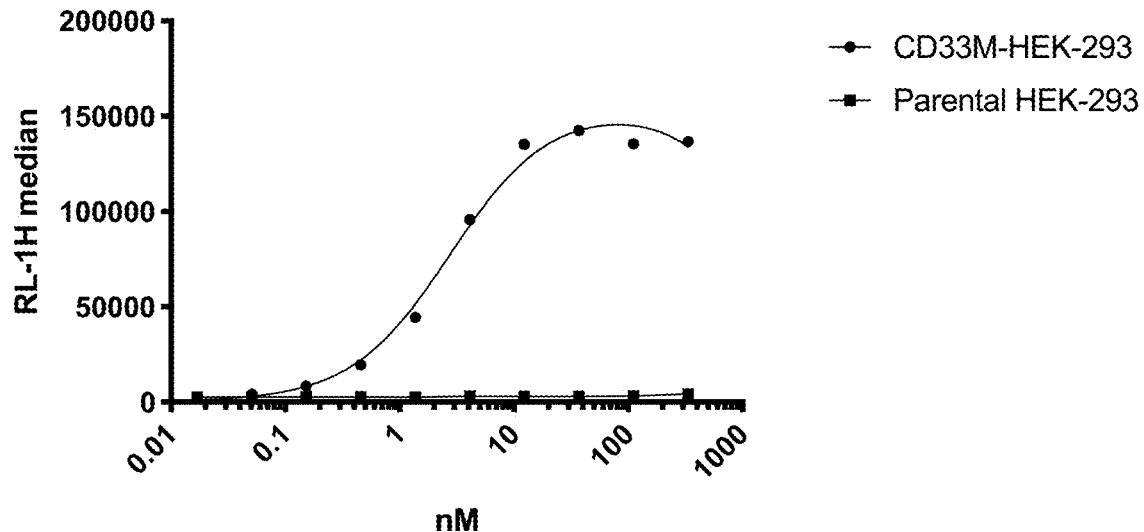
Figure 2L:
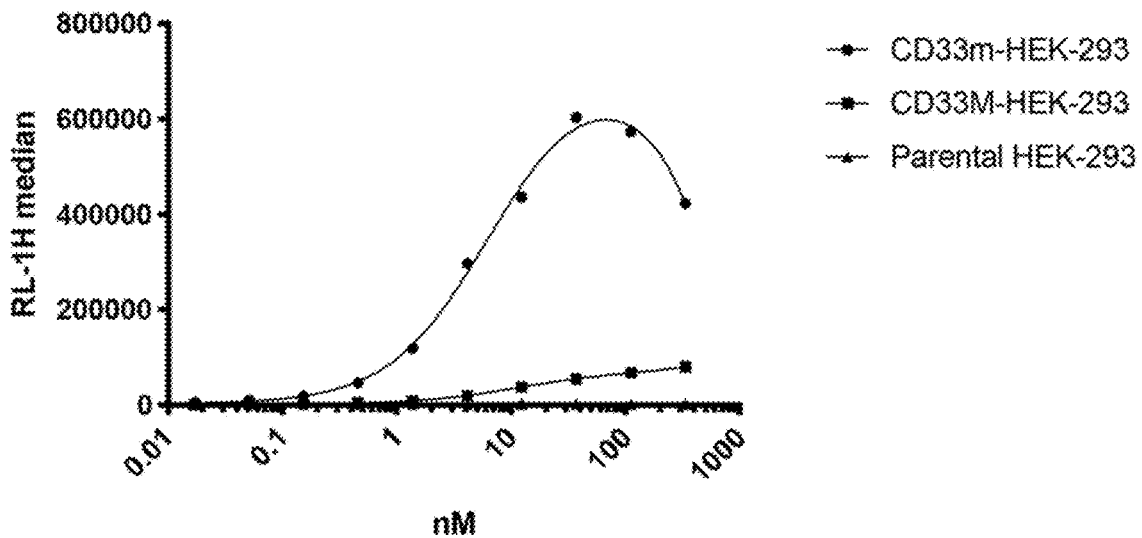
Figure 2M:
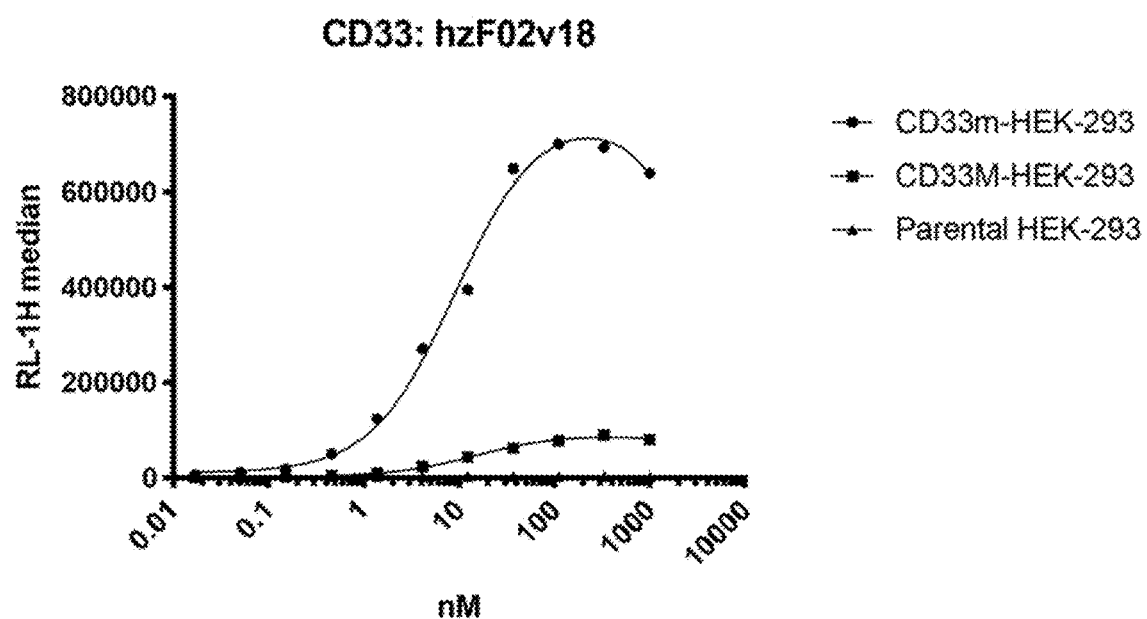

Embodiments provided herein relate to CD33-binding polypeptides and their use in various methods of treating cancer.

Definitions and Various Embodiments

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The phrase "reference sample", "reference cell", or "reference tissue", denote a sample with at least one known characteristic that can be used as a comparison to a sample with at least one unknown characteristic. In some embodiments, a reference sample can be used as a positive or negative indicator. A reference sample can be used to establish a level of protein and/or mRNA that is present in, for example, healthy tissue, in contrast to a level of protein and/or mRNA present in the sample with unknown characteristics. In some embodiments, the reference sample comes from the same subject, but is from a different part of the subject than that being tested. In some embodiments, the reference sample is from a tissue area surrounding or adjacent to the cancer. In some embodiments, the reference sample is not from the subject being tested, but is a sample from a subject known to have, or not to have, a disorder in question (for example, a particular cancer or CD33-related disorder). In some embodiments, the reference sample is from the same subject, but from a point in time before the subject developed cancer. In some embodiments, the reference sample is from a benign cancer sample, from the same or a different subject. When a negative reference sample is used for comparison, the level of expression or amount of the molecule in question in the negative reference sample will indicate a level at which one of skill in the art will appreciate, given the present disclosure, that there is no and/or a low level of the molecule. When a positive reference sample is used for comparison, the level of expression or amount of the molecule in question in the positive reference sample will indicate a level at which one of skill in the art will appreciate, given the present disclosure, that there is a level of the molecule.

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (that is, reduction, slowing down or complete stopping) of disease cell infiltration into adjacent peripheral organs and/or tissues; inhibition (that is, reduction, slowing down or complete stopping) of disease spread; relief, to some extent, of one or more symptoms associated with the disorder; increase in the length of disease-free presentation following treatment, for example, progression-free survival; increased overall survival; higher response rate; and/or decreased mortality at a given point of time following treatment. A subject or cancer that is "non-responsive" or "fails to respond" is one that has failed to meet the above noted qualifications to be "responsive".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"CD33" as used herein refers to any native, mature CD33 that results from processing of a CD33 precursor in a cell. The term includes CD33 from any vertebrate source, including mammals such as primates (e.g., humans and cynomolgus or rhesus monkeys) and rodents (e.g., mice and rats), unless otherwise indicated. The term also includes naturally-occurring variants of CD33, such as splice variants or allelic variants. A nonlimiting exemplary human CD33 amino acid sequence is shown, e.g., in UniProt Accession No. P20138. A mature form of CD33 may lack a signal peptide (for example, a mature form of CD33 may lack amino acids 1-17 of UniProt Accession No. P20138). See SEQ ID NO. 1.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a CD33 epitope is a sdAb or VHH-containing polypeptide that binds this epitope with greater affinity, avidity, more readily, and/or with greater duration than it binds to other CD33 epitopes or non-CD33 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time. As used herein, the term "inhibit" with regard to the activity of CD33 refers to a decrease in an activity of CD33, such as binding to a sialic acid. In some embodiments, "inhibit" refers to a decrease in a CD33 activity compared to the CD33 activity in the absence of the modulator. In some embodiments, a CD33-binding polypeptide described herein inhibits binding of CD33 to a sialic acid.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The term "antibody" is used in the broadest sense and encompass various polypeptides that comprise antibody-like antigen-binding domains, including but not limited to conventional antibodies (typically comprising at least one heavy chain and at least one light chain), single-domain antibodies (sdAbs, comprising at least one VHH domain and an Fc region), VHH-containing polypeptides (polypeptides comprising at least one VHH domain), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc regions (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "antigen-binding domain" as used herein refers to a portion of an antibody sufficient to bind antigen. In some embodiments, an antigen binding domain of a conventional antibody comprises three heavy chain CDRs and three light chain CDRs. Thus, in some embodiments, an antigen binding domain comprises a heavy chain variable region comprising CDR1-FR2-CDR2-FR3-CDR3, and any portions of FR1 and/or FR4 required to maintain binding to antigen, and a light chain variable region comprising CDR1-FR2-CDR2-FR3-CDR3, and any portions of FR1 and/or FR4 required to maintain binding to antigen. In some embodiments, an antigen-binding domain of an sdAb or VHH-containing polypeptide comprises three CDRs of a VHH domain. Thus, in some embodiments, an antigen binding domain of an sdAb or VHH-containing polypeptide comprises a VHH domain comprising CDR1-FR2-CDR2-FR3-CDR3, and any portions of FR1 and/or FR4 required to maintain binding to antigen.

The term "VHH" or "VHH domain" or "VHH antigen-binding domain" as used herein refers to the antigen-binding portion of a single-domain antibody, such as a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprises only a partial FR1 and/or FR4, or lacks one or both of those framework regions, so long as the VHH substantially maintains antigen binding and specificity.

The terms "single domain antibody" and "sdAb" are used interchangeably herein to refer to an antibody comprising at least one monomeric domain, such as a VHH domain, without a light chain, and an Fc region. In some embodiments, an sdAb is a dimer of two polypeptides wherein each polypeptide comprises at least one VHH domain and an Fc region. As used herein, the terms "single domain antibody" and "sdAb" encompass polypeptides that comprise multiple VHH domains, such as a polypeptide having the structure $VHH_1$-$VHH_2$-Fc or $VHH_1$-$VHH_2$-$VHH_3$-Fc, wherein $VHH_1$, $VHH_2$, and $VHH_3$ may be the same or different.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc region. In some such embodiments, the VHH-containing polypeptide may be referred to as an sdAb. Further, in some such embodiments, the VHH polypeptide may form a dimer. Nonlimiting structures of VHH-containing polypeptides, which are also sdAbs, include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

"Affinity" refers to the strength of the sum total of noncovalent interactions between a single binding site of a molecule (for example, an antibody, such as an sdAb, or VHH-containing polypeptide) and its binding partner (for example, an antigen). The affinity or the apparent affinity of a molecule X for its partner Y can generally be represented by the dissociation constant ($K_d$) or the $K_{d\text{-}apparent}$, respectively. Affinity can be measured by common methods known in the art (such as, for example, ELISA $K_d$, KinExA, flow cytometry, and/or surface plasmon resonance devices), including those described herein. Such methods include, but are not limited to, methods involving BIAcore®, Octet®, or flow cytometry.

The term "$K_d$", as used herein, refers to the equilibrium dissociation constant of an antigen-binding molecule/antigen interaction. When the term "$K_d$" is used herein, it includes $K_d$ and $K_{d\text{-}apparent}$.

In some embodiments, the $K_d$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_d$ is $K_d$-apparent.

The term "biological activity" refers to any one or more biological properties of a molecule (whether present naturally as found in vivo, or provided or enabled by recombinant means).

An "agonist" or "activating" antibody is one that increases and/or activates a biological activity of the target antigen. In some embodiments, the agonist antibody binds to an antigen and increases its biologically activity by at least about 20%, 40%, 60%, 80%, 85% or more.

An "antagonist", a "blocking" or "neutralizing" antibody is one that inhibits, decreases and/or inactivates a biological activity of the target antigen. In some embodiments, the neutralizing antibody binds to an antigen and reduces its biologically activity by at least about 20%, 40%, 60%, 80%, 85% 90%, 95%, 99% or more.

An "affinity matured" sdAb or VHH-containing polypeptide refers to a sdAb or VHH-containing polypeptide with one or more alterations in one or more CDRs compared to a parent sdAb or VHH-containing polypeptide that does not possess such alterations, such alterations resulting in an improvement in the affinity of the sdAb or VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize sdAb VHH-containing polypeptide performance. In some embodiments, a humanized sdAb or VHH-containing polypeptide comprises a human Fc region. As will be appreciated, a humanized sequence can be identified by its primary sequence and does not necessarily denote the process by which the antibody was created.

An "effector-positive Fc region" possesses an "effector function" of a native sequence Fc region. Exemplary "effector functions" include Fc receptor binding; C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology,* 15(7):637-640 (1997); Hinton et al., *J Biol. Chem.* 279(8):6213-6216 (2004); WO 2004/92219 (Hinton et al.).

A "chimeric antigen receptor" as used herein refers to an engineered polypeptide that comprises an extracellular antigen recognition domain, a transmembrane domain, and an intracellular signaling domain. In some embodiments, the extracellular antigen recognition domain comprises a VHH domain.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |

TABLE 1-continued

| Original Residue | Exemplary Substitutions |
| --- | --- |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, hematologic cancers such as leukemias, lymphomas, and multiple myelomas, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; acute myeloid leukemia (AML); chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" or "non-cancer cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering a therapeutic agent. "Ameliorating" also includes shortening or reduction in duration of a symptom.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" in the context of an experiment or comparison, refers to a composition known to not contain an analyte ("negative control") or to contain an analyte ("positive control"). A positive control can comprise a known concentration of analyte. A control or reference may also refer to a control agent known to lack the activity of an agent being tested, such as an antibody.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms "pharmaceutical formulation" and "pharmaceutical composition" are used interchangeably and refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effects of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Exemplary CD33-Binding Polypeptides

CD33-binding polypeptides are provided herein. In various embodiments, the CD33-binding polypeptides comprise at least one VHH domain that binds CD33. In some embodiments, the CD33 is a human CD33. In some embodiments, a CD33-binding polypeptide blocks binding of CD33 to a sialic acid. In some embodiments, a CD33-binding polypeptide provided herein comprises one, two, three, four, five, six, seven, or eight VHH domains that bind CD33. In some embodiments, a CD33-binding polypeptide provided herein comprises one, two, three, or four VHH domains that bind CD33. CD33-binding polypeptides may comprise one or more VHH domains that bind one or more target proteins other than CD33. Such polypeptides may be referred to as "multispecific" polypeptides.

In some embodiments, a CD33-binding polypeptide comprises at least one VHH domain that binds CD33 and an Fc region. In some embodiments, a CD33-binding polypeptide provided herein comprises one, two, three, or four VHH domains and an Fc region. In some embodiments, an Fc region mediates dimerization of the CD33-binding polypeptide at physiological conditions such that a dimer is formed that doubles the number of CD33 binding sites. For example, a CD33-binding polypeptide comprising three VHH domains that bind CD33 and an Fc region is trivalent as a monomer, but at physiological conditions, the Fc region may mediate dimerization, such that the CD33-binding polypeptide exists as a hexavalent dimer under such conditions.

In some embodiments, a CD33-binding polypeptide comprises at least two VHH domains, wherein a first VHH domain binds a first epitope of CD33 and a second VHH domain binds a second epitope of CD33. When the CD33-binding polypeptide comprises a VHH domain that binds a first epitope of CD33 and a VHH domain that binds a second epitope of CD33, the CD33-binding polypeptide may be referred to as "biepitopic" or "bispecific." In some embodiments, a CD33-binding polypeptide comprises at least two VHH domains, wherein a first VHH domain binds CD33 and a second VHH domain binds an antigen other than CD33. Such polypeptides may be referred to as "bispecific" or "multispecific."

Nonlimiting exemplary CD33-binding polypeptides are shown in Table 2. The sequences for the indicated single-domain antibodies are shown in the Table of Certain Sequences herein. A polypeptide name that begins with "hz" indicates that it is a humanized version of the corresponding parental polypeptide.

TABLE 2

Polypeptides comprising at least one VHH that binds CD33

| Name | CDRs | VHH (or KP version or SS version) |
|---|---|---|
| A07 | SEQ ID NOs: 3, 4, and 5 | SEQ ID NO: 2 (or 123) |
| 401-A9 | SEQ ID NOs: 7, 8, and 9 | SEQ ID NO: 6 (or 131) |
| B07 | SEQ ID NOs: 11, 12, and 13 | SEQ ID NO: 10 (or 124) |
| 1C7 | SEQ ID NOs: 15, 16, and 17 | SEQ ID NO: 14 (or 125) |
| 1E4 | SEQ ID NOs: 19, 20, and 21 | SEQ ID NO: 18 (or 126) |

TABLE 2-continued

Polypeptides comprising at least one VHH that binds CD33

| Name | CDRs | VHH (or KP version or SS version) |
|---|---|---|
| F02 | SEQ ID NOs: 23, 24, and 25 | SEQ ID NO: 22 (or 127) |
| 1G3 | SEQ ID NOs: 27, 28, and 29 | SEQ ID NO: 26 (or 128) |
| G11 | SEQ ID NOs: 31, 32, and 33 | SEQ ID NO: 30 (or 129) |
| 1H9 | SEQ ID NOs: 35, 36, and 37 | SEQ ID NO: 34 (or 130) |
| hzA07v4 | SEQ ID NOs: 47, 48, and 49 | SEQ ID NO: 38 (or 114) |
| hzB07v7 | SEQ ID NOs: 50, 51, and 52 | SEQ ID NO: 39 (or 115) |
| hz1C7v1 | SEQ ID NOs: 53, 54, and 55 | SEQ ID NO: 40 (or 116) |
| hz1C7v11 | SEQ ID NOs: 56, 57, and 58 | SEQ ID NO: 41 (or 117) |
| hz1E4v2 | SEQ ID NOs: 59, 60, and 61 | SEQ ID NO: 42 (or 118) |
| hzF02v18 | SEQ ID NOs: 62, 63, and 64 | SEQ ID NO: 43 (or 119) |
| hz1G3v3 | SEQ ID NOs: 65, 66, and 67 | SEQ ID NO: 44 (or 120) |
| hzG11v2 | SEQ ID NOs: 68, 69, and 70 | SEQ ID NO: 45 (or 121) |
| hz1H9v2 | SEQ ID NOs: 71, 72, and 73 | SEQ ID NO: 46 (or 122) |

CD33-Binding Polypeptides

In various embodiments, a VHH domain that binds CD33 comprises a CDR1 sequence selected from SEQ ID NOs: 3, 7, 11, 15, 19, 23, 27, 31, 35, 47, 50, 53, 56, 59, 62, 65, 68, and 71; a CDR2 sequence selected from SEQ ID NOs: 4, 8, 12, 16, 20, 24, 28, 32, 36, 48, 51, 54, 57, 60, 63, 66, 69, and 72; and a CDR3 sequence selected from SEQ ID NOs: 5, 9, 13, 17, 21, 25, 29, 33, 37, 49, 52, 55, 58, 61, 64, 67, 70, and 73. In various embodiments, a VHH domain that binds CD33 comprises CDR1, CDR2, and CDR3 sequences selected from: SEQ ID NOs: 3, 4, and 5; SEQ ID NOs: 7, 8, and 9; SEQ ID NOs: 11, 12, and 13; SEQ ID NOs: 15, 16, and 17; SEQ ID NOs: 19, 20, and 21; SEQ ID NOs: 23, 24, and 25; SEQ ID NOs: 27, 28, and 29; SEQ ID NOs: 31, 32, and 33; SEQ ID NOs: 35, 36, and 37; SEQ ID NOs: 47, 48, and 49; SEQ ID NOs: 50, 51, and 52; SEQ ID NOs: 53, 54, and 55; SEQ ID NOs: 56, 57, and 58; SEQ ID NOs: 59, 60, and 61; SEQ ID NOs: 62, 63, and 64; SEQ ID NOs: 65, 66, and 67; SEQ ID NOs: 68, 69, and 70; and SEQ ID NOs: 71, 72, and 73. In various embodiments, the VHH domain is humanized.

In some embodiments, a VHH domain that binds CD33 comprises an amino acid sequence that is at least 85%, at least 90%, at least 95%, at least 96%, at least 97%, at least 98%, at least 99% identical to an amino acid sequence selected from SEQ ID NOs: 2, 6, 10, 14, 18, 22, 26, 30, 34, 38, 39, 40, 41, 42, 43, 44, 45, 46, 114, 115, 116, 117, 118, 119, 120, 121, 122, 123, 124, 125, 126, 127, 128, 129, 130, and 131. In some embodiments, a VHH domain that binds CD33 comprises an amino acid sequence selected from SEQ ID NOs: 2, 6, 10, 14, 18, 22, 26, 30, 34, 38, 39, 40, 41, 42, 43, 44, 45, 46, 114, 115, 116, 117, 118, 119, 120, 121, 122, 123, 124, 125, 126, 127, 128, 129, 130, and 131.

In various embodiments, a CD33-binding polypeptide comprises one, two, three, or four VHH domains that bind CD33.

In various embodiments, CD33-binding polypeptide comprises at least one VHH domain that binds CD33 and at least one VHH domain that binds a natural killer cell antigen or a T-cell antigen. In some such embodiments, the CD33-binding polypeptide may be referred to as a multispecific antibody.

In some embodiments, a CD33 binding polypeptide comprises at least one VHH domain described herein fused to an Fc region. In some embodiments, the Fc region has a sequence selected from SEQ ID NOs: 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, and 109.

In some embodiments, a VHH domain that binds CD33 may be humanized. Humanized antibodies (such as sdAbs or VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005)Methods 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

In various embodiments, an Fc region included in a CD33-binding polypeptide is a human Fc region, or is derived from a human Fc region.

In some embodiments, an Fc region included in a CD33-binding polypeptide is derived from a human Fc region, and comprises a three amino acid deletion in the lower hinge corresponding to IgG1 E233, L234, and L235, herein referred to as "Fc xELL." Fc xELL polypeptides do not engage FcγRs and thus are referred to as "effector silent" or "effector null", however in some embodiments, xELL Fc regions bind FcRn and therefore have extended half-life and transcytosis associated with FcRn mediated recycling.

In some embodiments, the Fc region included in a CD33-binding polypeptide is derived from a human Fc region and comprises mutations M252Y and M428V, herein referred to as "Fc-YV". In some embodiments, such mutations enhance binding to FcRn at the acidic pH of the endosome (near 6.5), while losing detectable binding at neutral pH (about 7.2), allowing for enhanced FcRn mediated recycling and extended half-life.

In some embodiments, the Fc region included in a CD33-binding polypeptide is derived from a human Fc region and comprises mutations designed for heterodimerization, herein referred to as "knob" and "hole". In some embodiments, the "knob" Fc region comprises the mutation T366W. In some embodiments, the "hole" Fc region comprises mutations T366S, L368A, and Y407V. In some embodiments, Fc regions used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hold Fc region comprises the modification H435R or H435K (referred to as "hole-R" in some instances when the modification is H435R), while the knob Fc region does not. In some instances, the hole-R mutation improves purification of the heterodimer over homodimeric hole Fc regions that may be present.

Nonlimiting exemplary Fc regions that may be used in a CD33-binding polypeptide include Fc regions comprising the amino acid sequences of SEQ ID NOs: 74 to 109.

Chimeric Receptors and Engineered Cells

Provided herein are chimeric antigen receptors (CARs) having an extracellular domain comprising one or more of the CD33-binding VHH domains provided herein. CAR constructs provided herein include an extracellular domain containing the one or more CD33-binding VHH domain, a transmembrane domain and an intracellular signaling region. The one or more CD33-binding VHH domain which form the antigen binding unit of the CAR binds or is capable of binding, i.e. targets, CD33-binding with sufficient affinity such the CAR is useful in therapy in targeting a cell or tissue expressing CD33-binding.

CARs are synthetic receptors typically containing an extracellular targeting/binding moiety that is associated with one or more signaling domains in a single fusion molecule that is expressed on the surface of a cell, such as a T cell. Thus, CARs combine antigen-specificity and T cell activating properties in a single fusion molecule. First generation CARs typically included the cytoplasmic region of the CD3zeta or Fc 1 receptor γ chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signaling domains of a costimulatory molecule, such as CD28, and CD3zeta, provide dual signaling to direct combined activating and co-stimulatory signals. Third generation CARs are more complex with three or more signaling domains (reviewed in Sadelain et al., Cancer Discovery (3), 388-398, 2013 and Dotti et al, Immuno. Rev, 257 (1), 1-36, 2014).

In some embodiments, a provided CAR comprises a CD33-binding VHH domain. In some embodiments, the CAR contains at least two VHH domains that target one or more antigen. In one embodiment, the antigen binding domain of a CAR comprises two or at least two CD33-binding VHH domains, thus providing a bivalent molecule. In one embodiment, the antigen binding domain comprises two or at least two CD33-binding VHH domains, but bind to different epitopes on CD33. In such cases, the antigen binding domain comprises a first CD33-binding VHH domain that binds to a first epitope of CD33 and a second VHH domain that binds to a second epitope of CD33. The epitopes may be overlapping. Thus, in some embodiments, the antigen binding domain is biparatopic and the CAR is a biparatopic CAR. In yet another embodiment, the antigen binding domain comprises two CD33-binding VHH domains that bind to the same epitopes on CD33.

The transmembrane domain of a CAR provided herein is a domain that typically crosses or is capable of crossing or spanning the plasma membrane and is connected, directly or indirectly (e.g. via a spacer, such as an immunoglobulin hinge sequence) to the extracellular antigen binding domain and the endoplasmic portion containing the intracellular signaling domain. In one embodiment, the transmembrane domain of the CAR is a transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from ζ chain of the T-cell receptor complex or any of its homologs (e.g., η chain, FcsRIy and β chains, MB 1 (Iga) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-IBB), CD134 (OX40), Dap10, CD27, CD2, CD5, ICAM-1, LFA-1 (CD1 1a/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-IBB).

In some embodiments, the costimulatory signaling domain is a derived from CD28 or 41BB.

In particular embodiments, the CAR further comprises a hinge or spacer region which connects the extracellular antigen binding domain and the transmembrane domain. This hinge or spacer region can be used to achieve different lengths and flexibility of the resulting CAR. Examples of the a hinge or spacer region that can be used include, but are not limited to, Fc fragments of antibodies or fragments or derivatives thereof, hinge regions of antibodies, or fragments or derivatives thereof, CH2 regions of antibodies, CH3 regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8.

Also provided herein is an isolated nucleic acid construct comprising at least one nucleic acid encoding a CAR as provided herein. In some aspects, the construct is an expression vector for expression of the CAR in a cell. The expression vector may be a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express a CAR provided herein. Thus, provided herein are genetically engineered cells which comprise, such as stably express, a CAR provided herein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some cases, the cell is a T cell, such as a CD4 and/or CD8 T cell. In some embodiments, the cells are autologous to the subject. For example, in some embodiments, T cells may be isolated from a patient (also called primary T cells) for engineering, e.g. transfection or transduction, with a CAR nucleic acid construct.

In an exemplary example, primary T-cells can be purified ex vivo (CD4 cells or CD8 cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for CAR expression by, for example, flow cytometry using anti-epitope tag or antibodies that cross-react with native parental molecule. T-cells that express the CAR can be enriched through sorting with anti-epitope tag antibodies or enriched for high or low expression depending on the application.

The CAR engineered T-cells can be assayed for appropriate function by a variety of means. In some cases, in vitro cytotoxicity, proliferation, or cytokine assays (e.g., IFN-gamma expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Polypeptide Expression and Production

Nucleic acid molecules comprising polynucleotides that encode a CD33-binding polypeptide are provided. In some embodiments, the nucleic acid molecule may also encode a leader sequence that directs secretion of the CD33-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the CD33-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In some embodiments, a CD33-binding polypeptide may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the CD33-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses a CD33-binding polypeptide described herein is provided. The CD33-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify a CD33-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the CD33-binding polypeptide is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

In some embodiments, CD33-binding polypeptides prepared by the methods described above are provided. In some embodiments, the CD33-binding polypeptide is prepared in a host cell. In some embodiments, the CD33-binding polypeptide is prepared in a cell-free system. In some embodiments, the CD33-binding polypeptide is purified. In some embodiments, a cell culture media comprising a CD33-binding polypeptide is provided.

In some embodiments, compositions comprising antibodies prepared by the methods described above are provided. In some embodiments, the composition comprises a CD33-binding polypeptide prepared in a host cell. In some embodiments, the composition comprises a CD33-binding polypeptide prepared in a cell-free system. In some embodiments, the composition comprises a purified CD33-binding polypeptide.

Exemplary Methods of Treating Diseases Using CD33-Binding Polypeptides

In some embodiments, methods of treating disease in an individual comprising administering a CD33-binding polypeptide or cells expressing a CD33-binding polypeptide are provided. In some embodiments, methods for treating cancer in an individual are provided. In some embodiments, methods for treating CD33-expressing or CD33-positive cancer in an individual are provided. The method comprises administering to the individual an effective amount of a CD33-binding polypeptide or cells expressing a CD33-binding polypeptide provided herein. In some embodiments, the CD33-binding polypeptide blocks binding of CD33 to a sialic acid. In some embodiments, the CD33-binding polypeptide is used to bring a cytotoxic agent to a CD33-expressing cell. In some such embodiments, the CD33-binding polypeptide comprises a binding domain that binds a cytotoxic T cell or NK cell. In some such embodiments, the binding domain binds CD3, T-cell receptor (TCR) α, TCRβ, CD28, CD16, CD32A, CD64, CD89, NKp46, or NKG2D. The binding domain may be, in some embodiments, a VHH domain or an antibody binding domain comprising a heavy chain variable region and a light chain variable region, such as a VH/VL, scFv, Fab fragment, etc.

In some embodiments, the CD33-binding polypeptide is linked to a cytotoxic agent to form an immunoconjugate. Various cytotoxic agents used in immunoconjugates are known in the art, and include, but are not limited to, calicheamicins, auristatins, dolastatins, tubulicins, maytansinoids, cryptophycins, duocarmycins, esperamicins, pyrrolobenzodiazepines, and enediyne antibiotics.

In some embodiments, the CD33-binding polypeptide is a chimeric antigen receptor expressed on a cytotoxic cell, such as a T cell (CAR-T) or NK cell (CAR-NK). Such methods of treatment may be in humans or animals. In some embodiments, methods of treating humans are provided.

Nonlimiting exemplary cancers that may be treated with CD33-binding polypeptides or cells expressing CD33-binding polypeptides provided herein include, but are not limited to, lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; acute myeloid leukemia (AML); chronic lymphocytic leukemia (CLL); acute lymphoblastic leukemia (ALL); Hairy cell leukemia; chronic myeloblastic leukemia. In some embodiments, the cancer is a CD33-expressing (i.e., CD33-positive) cancer.

The CD33-binding polypeptides or cells expressing CD33-binding polypeptides can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of a CD33-binding polypeptides or cells expressing CD33-binding polypeptides is administered to a subject one or more times. In some embodiments, an effective dose of a CD33-binding polypeptides or cells expressing CD33-binding polypeptides is administered to the subject daily, semiweekly, weekly, every two weeks, once a month, etc. An effective dose of a CD33-binding polypeptides or cells expressing CD33-binding polypeptides is administered to the subject at least once. In some embodiments, the effective dose of a CD33-binding polypeptide or cells expressing a CD33-binding polypeptide may be administered multiple times, including multiple times over the course of at least a month, at least six months, or at least a year.

In some embodiments, pharmaceutical compositions are administered in an amount effective for treating (including prophylaxis of) cancer. The therapeutically effective amount is typically dependent on the weight of the subject being treated, his or her physical or health condition, the extensiveness of the condition to be treated, or the age of the subject being treated. In general, antibodies may be administered in an amount in the range of about 0.05 mg/kg body weight to about 100 mg/kg body weight per dose. In some embodiments, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose. In some embodiments, antibodies may be administered in an amount in the range of about 0.5 mg/kg body weight to about 10 mg/kg body weight per dose. In some embodiments, antibodies may be administered in an amount in the range of about 0.05 mg/kg body weight to about 20 mg/kg body weight per dose. In some embodiments, antibodies may be administered in an amount in the range of about 0.05 mg/kg body weight to about 10 mg/kg body weight per dose. In some embodiments, antibodies may be administered in an amount in the range of about 5 mg/kg body weight or lower, for example less than 4, less than 3, less than 2, or less than 1 mg/kg of the antibody.

In some embodiments, CD33-binding polypeptides or cells expressing CD33-binding polypeptides can be administered in vivo by various routes, including, but not limited to, intravenous, intra-arterial, parenteral, intraperitoneal or subcutaneous. The appropriate formulation and route of administration may be selected according to the intended application.

In some embodiments, a therapeutic treatment using a CD33-binding polypeptide is achieved by targeting a cytotoxic agent to a CD33-expressing cell, such as a CD33-expressing cancer cell. In some such embodiments, the CD33-binding polypeptide is a chimeric antigen receptor expressed on a cytotoxic cell, such as a T cell or NK cell.

Pharmaceutical Compositions

In some embodiments, compositions comprising CD33-binding polypeptides are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7$^{th}$ ed., Lippencott Williams and Wilkins (2004); Kibbe et al., Handbook of Pharmaceutical Excipients, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprises a CD33-binding polypeptide at a concentration of at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL.

Combination Therapy

CD33-binding polypeptides or engineered cells of the present disclosure can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a CD33-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as VISTA, gpNMB, B7H4, HHLA2, CD73, CTLA4, TIGIT, etc.

In some embodiments, the CD33-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies. BMS-936558), PDL1 inhibitors (e.g. anti-PDL1 antibodies, MPDL3280A), PDL2 inhibitors (e.g., anti-PDL2 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a CD33-binding polypeptide or engineered cell provided herein is given concurrently with a PD-1/or PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the CD33-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.,* 33: 183-186 (1994)); dynemicin, including dynemicin A;

bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Illinois), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LURTOTECAN® topoisomerase 1 inhibitor; ABARELIX® GnRH agoninst; and pharmaceutically acceptable salts, acids or derivatives of any of the above.

In some embodiments, the CD33-binding polypeptide and the additional agent are formulated into a single therapeutic composition, and the CD33-binding polypeptide and additional agent are administered simultaneously. Alternatively, the CD33-binding polypeptide or engineered cell and the additional agent are separate from each other, e.g., each is formulated into a separate therapeutic composition, and the CD33-binding polypeptide or engineered cell and the additional agent are administered simultaneously, or the CD33-binding polypeptide or engineered cell and the additional agent are administered at different times during a treatment regimen. For example, the CD33-binding polypeptide or engineered cell is administered prior to the administration of the additional agent, the CD33-binding polypeptide or engineered cell is administered subsequent to the administration of the additional agent, or the CD33-binding polypeptide or engineered cell and the additional agent are administered in an alternating fashion. The CD33-binding polypeptide and additional agent may be administered in single doses or in multiple doses.

In some embodiments, the CD33-binding polypeptide or engineered cell and the additional agent(s) are administered simultaneously. For example, the CD33-binding polypeptide and the additional agent(s) can be formulated in a single composition or administered as two or more separate compositions. In some embodiments, the CD33-binding polypeptide or engineered cell and the additional agent(s) are administered sequentially, or the CD33-binding polypeptide or engineered cell and the additional agent are administered at different times during a treatment regimen.

Nonlimiting Exemplary Methods of Diagnosis and Treatment

In some embodiments, the methods described herein are useful for evaluating a subject and/or a specimen from a subject (e.g. a cancer patient). In some embodiments, evaluation is one or more of diagnosis, prognosis, and/or response to treatment.

In some embodiments, the methods described herein comprise evaluating a presence, absence, or level of a protein. In some embodiments, the methods described herein comprise evaluating a presence, absence, or level of expression of a nucleic acid. The compositions described herein may be used for these measurements. For example, in some embodiments, the methods described herein comprise contacting a specimen of the tumor or cells cultured from the tumor with a therapeutic agent as described herein.

In some embodiments, the evaluation may direct treatment (including treatment with the antibodies described herein). In some embodiments, the evaluation may direct the use or withholding of adjuvant therapy after resection. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the polypeptides are used as an adjuvant therapy in the treatment of a cancer. In some embodiments, the polypeptides are used as the sole adjuvant therapy in the treatment of a cancer. In some embodiments, the polypeptides described herein are withheld as an adjuvant therapy in the treatment of a cancer. For example, if a patient is unlikely to respond to an antibody described herein or will have a minimal response, treatment may not be administered in the interest of quality of life and to avoid unnecessary toxicity from ineffective chemotherapies. In such cases, palliative care may be used.

In some embodiments the polypeptides are administered as a neoadjuvant therapy prior to resection. In some embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an antibody is administered to cancer patients prior to surgery. Types of cancers for which neoadjuvant chemotherapy is commonly considered include, for example, breast, colorectal, ovarian, cervical, bladder, and lung. In some embodiments, the polypeptides are used as a neoadjuvant therapy in the treatment of a cancer. In some embodiments, the use is prior to resection.

In some embodiments, the tumor microenvironment contemplated in the methods described herein is one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells; macrophages; other lymphoid cells; neutrophils; and other immune cells located proximal to a tumor.

Kits

Also provided are articles of manufacture and kits that include any of CD33-binding polypeptides as described herein, and suitable packaging. In some embodiments, the invention includes a kit with (i) a CD33-binding polypeptide, and (ii) instructions for using the kit to administer the CD33-binding polypeptide to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the antibodies generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or sub-unit doses. For example, kits may also be provided that contain sufficient dosages of molecules disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9 months, or more. Kits may also include multiple unit doses of molecules and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of antibody.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: CD33 Single-Domain Antibodies

Single domain antibodies targeting human CD33 were generated via immunization of llamas and alpaca with a recombinant version of the human CD33 extracellular domain.

Following the development of specific anti-CD33 antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. VHH sequences were specifically amplified via PCR using the cDNA as template and cloned into a yeast surface display vector as VHH-Fc-AGA2 fusion proteins.

Yeast libraries displaying the VHH-Fc-AGA2 fusion proteins were enriched using recombinant forms of the CD33 ECD via magnetic bead isolation followed by fluorescence activated cell sorting (FACS). Sorted yeast were plated out and isolated colonies were picked into 96-well blocks and grown in media that switched the expression from surface displayed VHH-Fc to secretion into the media. Supernatants from the 96-well yeast secretion cultures were applied to 293F cells transiently transfected with CD33 (CD33 positive) or untransfected 293F cells (CD33 negative), washed, treated with fluorophore labelled anti-human IgG1 Fc secondary antibody, and analyzed by 96-well flow cytometry.

Nucleic acid sequences encoding VHHs that bound to CD33 positive cells and not to CD33 negative cells were cloned in-frame with a human Fc encoding region into mammalian expression vectors, and expressed by transient transfection in HEK293 Freestyle cells (293F cells) or CHO cells using polyethylenimine. Supernatant was collected after 3-7 days, secreted recombinant protein was purified by protein A chromatography, and concentration was calculated from the absorbance at 280 nm and extinction coefficient.

The epitopes of single domain antibodies (sdAbs) that comprise VHH domains that bind CD33 were compared using Bio-Layer Interferometry. 7 ug/mL of AviTag™-histidine tagged human CD33 was immobilized on streptavidin coated capture sensors. 100 nM of one sdAb was then loaded onto the CD33 antigen and allowed to come to equilibrium. The sensors were then transferred into 100 nM of a second sdAb. An increase in assay signal represents binding, indicating that the second sdAb was targeting an epitope distinct from the epitope of the first sdAb.

Camelid-derived CD33 VHHs were humanized using the human VH3-23 germline as scaffold. Camelid residues that contribute to solubility, specificity, stability and/or affinity remained unmodified. Furthermore, where possible and as needed amino acid sequences that posse potential developability liabilities were modified to mitigate this risk. In addition all humanized variants contained the Leu11Glu (L11E) modification, as described in US20160207981.

The results indicate that one epitope was found among humanized versions of sdAbs 1E4, 1H9, 1G3, and 1C7. As shown in FIG. 1, hz1E4v2, hz1H9v2, hz1G3v3, and hz1C7v1 have a common epitope.

Example 2: Binding of Polypeptides to CD33

Binding of sdAbs to human CD33 was assessed by flow cytometry. Each sdAb comprised a VHH domain, as indicated in Table 3 below, and a human IgG1 xELL Fc region in which amino acids Glu233, Leu234, and Leu235, according to EU numbering, were deleted (SEQ ID NO: 75). MOLM-13 cells were transiently transfected with a plasmid encoding a sequence comprising "CD33M" (SEQ ID NO: 112) or a plasmid encoding a sequence comprising a truncated version, "CD33m" (SEQ ID NO: 113). The sequence encoded by the CD33M plasmid includes the leader sequence, full extracellular domain, transmembrane domain, and cytoplasmic domain. The sequence encoded by the CD33m plasmid includes the leader sequence, the membrane proximal IgC2 domain, and the transmembrane domain. Untransfected HEK 293 cells were used as CD33-negative cells. Each cell type was plated at 30,000 cells/well in FACS buffer (PBS 1% BSA, 0.1% NaN₃ pH 7.4) on a 96-well round-bottom plate. The sdAbs were diluted in FACS buffer in a 3-fold, 11 point serial dilution. The sdAb dilutions were added to the plated cells, and assay plates were incubated for 30 minutes at 4° C. After washing twice in 150 μL of FACS buffer, cells in each well were resuspended in 100 μL of 1:2000 Alexa Fluor 647-conjugated Anti-Human IgG secondary diluted in FACS buffer and incubated at 4° C. for 30 minutes. The cells were washed twice more, then bound antibody was detected by flow cytometry.

Flow cytometric analysis was performed on an Intellicyte iQue Plus and fluorescence was plotted as median fluorescence intensity. The apparent affinity ($K_d$, nM) was determined using one site binding non-linear regression in PRISM graph software.

As shown in FIGS. 2A to 2M, the tested sdAbs displayed CD33 binding and did not bind untransfected cells that do not express CD33. The apparent binding affinities are shown in Table 3 below.

TABLE 3

| sdAb | CD33 isoform | Apparent $K_d$ (nM) | SEQ ID NO of VHH domain |
|---|---|---|---|
| 1E4 | CD33M | 0.05 | 18 |
| hz1E4v2 | CD33M | 0.32 | 42 |
| 1H9 | CD33M | 0.14 | 34 |
| hz1H9v2 | CD33M | 0.27 | 46 |
| 1G3 | CD33M | 0.49 | 26 |
| hz1G3v3 | CD33M | 1.60 | 44 |
| 1C7 | CD33M | 6.64 | 14 |
| hz1C7v1 | CD33M | 6.25 | 40 |
| hz1C7v11 | CD33M | 5.45 | 41 |
| A07 | CD33M | 53.50 | 2 |
| A07 | CD33m | 19.90 | 2 |
| hzA07v4 | CD33M | 56.61 | 38 |
| hzA07v4 | CD33m | 11.76 | 38 |
| F02 | CD33M | 15.25 | 22 |
| F02 | CD33m | 5.15 | 22 |
| hzF02v18 | CD33M | 14.83 | 43 |
| hzF02v18 | CD33m | 9.13 | 43 |
| hzB07v7 | CD33M | 0.75 | 39 |
| G11 | CD33M | 1.1 | 30 |
| hzG11v2 | CD33M | 2.67 | 45 |

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

TABLE of Certain Sequences

| SEQ ID NO | Description | Sequence |
|---|---|---|
| 1 | Human CD33; mature form | DPNFWLQVQESVTVQEGLCVLVPCTFFHPIPYYDKNSPVHGYWFREGAII SRDSPVATNKLDQEVQEETQGRERLLGDPSRNNCSLSIVDARRRDNGSYF FRMERGSTKYSYKSPQLSVHVTDLTHRPKILIPGTLEPGHSKNLTCSVSW ACEQGTPPIFSWLSAAPTSLGPRTTHSSVLIITPRPQDHGTNLTCQVKFA GAGVTTERTIQLNVTYVPQNPTTGIFPGDGSGKQETRAGVVHGAIGGAGV TALLALCLCLIFFIVKTHRRKAARTAVGRNDTHPTTGSASPKHQKKSKLH GPTETSSCSGAAPTVEMDEELHYASLNFHGMNPSKDTSTEYSEVRTQ |
| 2 | A07 | QVQLVQSGGGLVQAGGSLTLSCAASRSSGIDVMGWYRQAPGKERELVAEISGV GDTNYAASLADRFTVSRDNAKNTVYLQMKNLKPEDTAVYYCNAHSFLDLVGAW GQGTQVTV |

TABLE-continued of Certain Sequences

| SEQ ID NO | Description | Sequence |
|---|---|---|
| 123 | A07 KP | QVQLVQSGGGLVQAGGSLTLSCAASRSSGIDVMGWYRQAPGKERELVAEISGV<br>GDTNYAASLADRFTVSRDNAKNTVYLQMKNLKPEDTAVYYCNAHSFLDLVGAW<br>GQGTQVTVKP |
| 3 | A07 CDR1 | RSSGIDVMG |
| 4 | A07 CDR2 | EISGVGDTN |
| 5 | A07 CDR3 | HSFLDLVGA |
| 6 | 401-A9 | QVQLQQSGGGLVQAGGSLRLSCAAPGSINSINVMEWYRQAPGKERDLVAGITS<br>DGDTNYVDSVPGRFTITRDNTMRTVDLQMNNLKADDTAVYYCRARDWGSLTDY<br>WGQGTQVTV |
| 131 | 401-A9 KP | QVQLQQSGGGLVQAGGSLRLSCAAPGSINSINVMEWYRQAPGKERDLVAGITS<br>DGDTNYVDSVPGRFTITRDNTMRTVDLQMNNLKADDTAVYYCRARDWGSLTDY<br>WGQGTQVTVKP |
| 7 | 401-A9 CDR1 | GSINSINVME |
| 8 | 401-A9 CDR2 | GITSDGDTN |
| 9 | 401-A9 CDR3 | RDWGSLTDY |
| 10 | B07 | EVQLVQSGGGLVQTGGSLRLSCGASGRTISDYVVGWFRQAPGKERAFVAAISR<br>YGTTYYAASVQGRFTISRDNPRNTVYLQVDSLRPEDTAVYFCAALQNDVRNNH<br>SPTSYDYWGQGTQVTV |
| 124 | B07 KP | EVQLVQSGGGLVQTGGSLRLSCGASGRTISDYVVGWFRQAPGKERAFVAAISR<br>YGTTYYAASVQGRFTISRDNPRNTVYLQVDSLRPEDTAVYFCAALQNDVRNNH<br>SPTSYDYWGQGTQVTVKP |
| 11 | B07 CDR1 | GRTISDYVVG |
| 12 | B07 CDR2 | AISRYGTTY |
| 13 | B07 CDR3 | LQNDVRNNHSPTSYDY |
| 14 | 1C7 | QVQLQQSGGGLVQAGGSLRLSCAASGRTFSGYIMGWFRQVPGKERELVARISG<br>NNLSTEYGGSVKGRFTISRDSAKETMYLQMNSLKPEDTAIYYCAAEYDYSSGD<br>FVYWGQGTQVTV |
| 125 | 1C7 KP | QVQLQQSGGGLVQAGGSLRLSCAASGRTFSGYIMGWFRQVPGKERELVARISG<br>NNLSTEYGGSVKGRFTISRDSAKETMYLQMNSLKPEDTAIYYCAAEYDYSSGD<br>FVYWGQGTQVTVKP |
| 15 | 1C7 CDR1 | GRTFSGYIMG |
| 16 | 1C7 CDR2 | RISGNNLSTE |
| 17 | 1C7 CDR3 | EYDYSSGDFVY |
| 18 | 1E4 | QVQLQQSGGGSVQAGGSLRLSCVASGSGFSASLMSWHRQAPGSQRDLVASITR<br>DGRANYVDSVKDRFTISRDNAKNTAYLQMDSLKPEDTAAYYCHAYSFDYPIRS<br>YWGQGTQVTV |
| 126 | 1E4 KP | QVQLQQSGGGSVQAGGSLRLSCVASGSGFSASLMSWHRQAPGSQRDLVASITR<br>DGRANYVDSVKDRFTISRDNAKNTAYLQMDSLKPEDTAAYYCHAYSFDYPIRS<br>YWGQGTQVTVKP |
| 19 | 1E4 CDR1 | GSGFSASLMS |
| 20 | 1E4 CDR2 | SITRDGRAN |
| 21 | 1E4 CDR3 | YSFDYPIRSY |
| 22 | F02 | QVQLVQSGGGLVQAGGSLRLSCAASGSISSYNVVGWYRQLSGNERGGRTMVAQ<br>INAYGDTNYANAVVGRFTISRDDAKNTVYLHMSNLKPEDTGVYYCNGQRMLEN<br>YTYRDQSWGQGTQVTV |
| 127 | F02 KP | QVQLVQSGGGLVQAGGSLRLSCAASGSISSYNVVGWYRQLSGNERGGRTMVAQ<br>INAYGDTNYANAVVGRFTISRDDAKNTVYLHMSNLKPEDTGVYYCNGQRMLEN<br>YTYRDQSWGQGTQVTVKP |

TABLE-continued of Certain Sequences

| SEQ ID NO | Description | Sequence |
|---|---|---|
| 23 | F02 CDR1 | GSISSYNVVG |
| 24 | F02 CDR2 | QINAYGDTN |
| 25 | F02 CDR3 | QRMLENYTYRDQS |
| 26 | 1G3 | EVQLQQSGGGEVQPGGSLRLSCEASGFTFSSYAMGWFRQAPGKGREWVAAITT SGDTTYYAESVKGRFTISRDNAKNTVYLQMSSLRAEDTAVYYCAAHRGGGVID YWGQGTQVTV |
| 128 | 1G3 KP | EVQLQQSGGGEVQPGGSLRLSCEASGFTFSSYAMGWFRQAPGKGREWVAAITT SGDTTYYAESVKGRFTISRDNAKNTVYLQMSSLRAEDTAVYYCAAHRGGGVID YWGQGTQVTVKP |
| 27 | 1G3 CDR1 | GFTFSSYAMG |
| 28 | 1G3 CDR2 | AITTSGDTTY |
| 29 | 1G3 CDR3 | HRGGGVIDY |
| 30 | G11 | EVQLVQSGGGSVQVGGSLRLSCAASGSTLNIDHIGWYRQAPGKERELVGVISS GAGPNYADSVKGRFTISRDNAKNTVYLQMNSLKPEDTAVYNCNAWIDYGSGLP QNYWGQGTQVTV |
| 129 | G11 KP | EVQLVQSGGGSVQVGGSLRLSCAASGSTLNIDHIGWYRQAPGKERELVGVISS GAGPNYADSVKGRFTISRDNAKNTVYLQMNSLKPEDTAVYNCNAWIDYGSGLP QNYWGQGTQVTVKP |
| 31 | G11 CDR1 | GSTLNIDHIG |
| 32 | G11 CDR2 | VISSGAGPN |
| 33 | G11 CDR3 | WIDYGSGLPQNY |
| 34 | 1H9 | EVQLQQSGGAVVQPGGSLRLSCAASGSIFSISIMGWYRQAPGKERELVASTTS SGTTNYVDSVKGRFTASRDNAKNTVYLQMNSLKPDDTAIYHCHAYIATTTDRG YRGYWGQGTQVTV |
| 130 | 1H9 KP | EVQLQQSGGAVVQPGGSLRLSCAASGSIFSISIMGWYRQAPGKERELVASTTS SGTTNYVDSVKGRFTASRDNAKNTVYLQMNSLKPDDTAIYHCHAYIATTTDRG YRGYWGQGTQVTVKP |
| 35 | 1H9 CDR1 | GSIFSISIMG |
| 36 | 1H9 CDR2 | STTSSGTTN |
| 37 | 1H9 CDR3 | YIATTTDRGYRGY |
| 38 | hzA07v4 | EVQLVESGGGEVQPGGSLRLSCAASRSSGIDVMGWYRQAPGKERELVAEISGV GDTNYAASLADRFTVSRDNAKNTVYLQMSSLRAEDTAVYYCNAHSFLDLVGAW GQGTLVTV |
| 114 | hzA07v4 KP | EVQLVESGGGEVQPGGSLRLSCAASRSSGIDVMGWYRQAPGKERELVAEISGV GDTNYAASLADRFTVSRDNAKNTVYLQMSSLRAEDTAVYYCNAHSFLDLVGAW GQGTLVTVKP |
| 39 | hzB07v7 | EVQLVESGGGEVQPGGSLRLSCAASGRTISDYVVGWFRQAPGKERAFVAAISR YGTTYYAASVQGRFTISRDNPRNTVYLQVDSLRAEDTAVYYCAALQNDVRNNH SPTSYDYWGQGTLVTV |
| 115 | hzB07v7 KP | EVQLVESGGGEVQPGGSLRLSCAASGRTISDYVVGWFRQAPGKERAFVAAISR YGTTYYAASVQGRFTISRDNPRNTVYLQVDSLRAEDTAVYYCAALQNDVRNNH SPTSYDYWGQGTLVTVKP |
| 40 | hz1C7v1 | EVQLVESGGGEVQPGGSLRLSCAASGRTFSGYIMGWFRQAPGKERELVARISG NNLSTEYAESVKGRFTISRDNAKNTLYLQMSSLRAEDTAVYYCAAEYDYSSGD FVYWGQGTLVTV |

TABLE-continued of Certain Sequences

| SEQ ID NO | Description | Sequence |
|---|---|---|
| 116 | hz1C7v1 KP | EVQLVESGGGEVQPGGSLRLSCAASGRTFSGYIMGWFRQAPGKERELVARISG NNLSTEYAESVKGRFTISRDNAKNTLYLQMSSLRAEDTAVYYCAAEYDYSSGD FVYWGQGTLVTVKP |
| 41 | hz1C7v11 | EVQLVESGGGEVQPGGSLRLSCAASGRTFSGYIMGWFRQAPGKERELVARISG NNLATEYAESVKGRFTISRDNAKNTLYLQMSSLRAEDTAVYYCAAEYDYSSGD FVYWGQGTLVTV |
| 117 | hz1C7v11 KP | EVQLVESGGGEVQPGGSLRLSCAASGRTFSGYIMGWFRQAPGKERELVARISG NNLATEYAESVKGRFTISRDNAKNTLYLQMSSLRAEDTAVYYCAAEYDYSSGD FVYWGQGTLVTVKP |
| 42 | hz1E4v2 | EVQLVESGGGEVQPGGSLRLSCAASGSGFSASLMSWHRQAPGKQRDLVASITR DGRANYVESVKGRFTISRDNAKNTLYLQMSSLRAEDTAVYYCHAYSFDYPIRS YWGQGTLVTV |
| 118 | hz1E4v2 KP | EVQLVESGGGEVQPGGSLRLSCAASGSGFSASLMSWHRQAPGKQRDLVASITR DGRANYVESVKGRFTISRDNAKNTLYLQMSSLRAEDTAVYYCHAYSFDYPIRS YWGQGTLVTVKP |
| 43 | hzF02v18 | EVQLVESGGGEVQPGGSLRLSCAASGSISSYNVMGWYRQAPGKQRELVAQINA YGDTNYANAVVGRFTISRDNAKNTVYLQMSSLRAEDTAVYYCNGQRMLENYTY RDQSWGQGTLVTV |
| 119 | hzF02v18 KP | EVQLVESGGGEVQPGGSLRLSCAASGSISSYNVMGWYRQAPGKQRELVAQINA YGDTNYANAVVGRFTISRDNAKNTVYLQMSSLRAEDTAVYYCNGQRMLENYTY RDQSWGQGTLVTVKP |
| 44 | hz1G3v3 | EVQLVESGGGEVQPGGSLRLSCAASGFTFSSYAMGWFRQAPGKGREWVAAITT SGDTTYYAESVKGRFTISRDNAKNTVYLQMSSLRAEDTAVYYCAAHRGGGVID YWGQGTLVTV |
| 120 | hz1G3v3 | EVQLVESGGGEVQPGGSLRLSCAASGFTFSSYAMGWFRQAPGKGREWVAAITT SGDTTYYAESVKGRFTISRDNAKNTVYLQMSSLRAEDTAVYYCAAHRGGGVID YWGQGTLVTVKP |
| 45 | hzG11v2 | EVQLVESGGGEVQPGGSLRLSCAASGSTLNIDHIGWYRQAPGKERELVGVISS GAGPNYAESVKGRFTISRDNAKNTVYLQMSSLRAEDTAVYYCNAWIDYGSGLP QNYWGQGTLVTV |
| 121 | hzG11v2 KP | EVQLVESGGGEVQPGGSLRLSCAASGSTLNIDHIGWYRQAPGKERELVGVISS GAGPNYAESVKGRFTISRDNAKNTVYLQMSSLRAEDTAVYYCNAWIDYGSGLP QNYWGQGTLVTVKP |
| 46 | hz1H9v2 | EVQLVESGGGEVQPGGSLRLSCAASGSIFSISIMGWYRQAPGKERELVASTTS SGTTNYVESVKGRFTISRDNAKNTLYLQMSSLRAEDTAVYYCHAYIATTTDRG YRGYWGQGTLVTV |
| 122 | hz1H9v2 KP | EVQLVESGGGEVQPGGSLRLSCAASGSIFSISIMGWYRQAPGKERELVASTTS SGTTNYVESVKGRFTISRDNAKNTLYLQMSSLRAEDTAVYYCHAYIATTTDRG YRGYWGQGTLVTVKP |
| 47 | CDR1 or hzA07v4 | RSSGIDVMG |
| 48 | CDR2 of hzA07v4 | EISGVGDTN |
| 49 | CDR3 of hzA07v4 | HSFLDLVGA |
| 50 | CDR1 or hzB07v7 | GRTISDYVVG |
| 51 | CDR2 of hzB07v7 | AISRYGTTY |
| 52 | CDR3 of hzB07v7 | LQNDVRNNHSPTSYDY |

TABLE-continued of Certain Sequences

| SEQ ID NO | Description | Sequence |
|---|---|---|
| 53 | CDR1 of hz1C7v1 | GRTFSGYIMG |
| 54 | CDR2 of hz1C7v1 | RISGNNLSTE |
| 55 | CDR3 of hz1C7v1 | EYDYSSGDFVY |
| 56 | CDR1 of hz1C7v11 | GRTFSGYIMG |
| 57 | CDR2 of hz1C7v11 | RISGNNLATE |
| 58 | CDR3 of hz1C7v11 | EYDYSSGDFVY |
| 59 | CDR1 of hz1E4v2 | GSGFSASLMS |
| 60 | CDR2 of hz1E4v2 | SITRDGRAN |
| 61 | CDR3 of hz1E4v2 | YSFDYPIRSY |
| 62 | CDR1 of hzF02v18 | GSISSYNVMG |
| 63 | CDR2 of hzF02v18 | QINAYGDTN |
| 64 | CDR3 of hzF02v18 | QRMLENYTYRDQS |
| 65 | CDR1 of hz1G3v3 | GFTFSSYAMG |
| 66 | CDR2 of hz1G3v3 | AITTSGDTTY |
| 67 | CDR3 of hz1G3v3 | HRGGGVIDY |
| 68 | CDR1 of hzG11v2 | GSTLNIDHIG |
| 69 | CDR2 of hzG11v2 | VISSGAGPN |
| 70 | CDR3 of hzG11v2 | WIDYGSGLPQNY |
| 71 | CDR1 of hz1H9v2 | GSIFSISIMG |
| 72 | CDR2 of hz1H9v2 | STTSSGTTN |
| 73 | CDR3 of hz1H9v2 | YIATTTDRGYRGY |
| 74 | human IgG1 Fc region | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHEAL HNHYTQKSLSLSPGK |
| 75 | human IgG1 xELL Fc region | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNH YTQKSLSLSPGK |

TABLE-continued of Certain Sequences

| SEQ ID NO | Description | Sequence |
|---|---|---|
| 76 | Fc region M252Y and M428V (YV) S354C T366W knob | DKTHTCPPCP APELLGGPSV FLFPPKPKDT LYISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPCRDELTK NQVSLWCLVK GFYPSDIAVE WESNGQPENN YKTTPPVLDS DGSFFLYSKL TVDKSRWQQG NVFSCSVVHE ALHNHYTQKS LSLSPGK |
| 77 | Fc region M252Y, M428V, H435R (YVR) T366S, L368A, Y407V hole | DKTHTCPPCP APELLGGPSV FLFPPKPKDT LYISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVCT LPPSRDELTK NQVSLSCAVK GFYPSDIAVE WESNGQPENN YKTTPPVLDS DGSFFLVSKL TVDKSRWQQG NVFSCSVVHE ALHNRYTQKS LSLSPGK |
| 78 | Fc region xELL H435R | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNRYTQK SLSLSPGK |
| 79 | Fc region xELL M252Y and M428V (YV) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNHYTQK SLSLSPGK |
| 80 | Fc region xELL M252Y and M428L (YL) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNHYTQK SLSLSPGK |
| 81 | Fc region xELL M252Y, M428L, H435R (YLR) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNRYTQK SLSLSPGK |
| 82 | Fc region xELL M252Y, M428V, H435R (YVR) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNRYTQK SLSLSPGK |
| 83 | Fc region xELL S354C T366W knob | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNHYTQK SLSLSPGK |
| 84 | Fc region xELL H435R S354C T366W knob | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNRYTQK SLSLSPGK |
| 85 | Fc region xELL M252Y and M428V (YV) S354C T366W knob | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVVHEALHNH YTQKSLSLSPGK |

TABLE-continued of Certain Sequences

| SEQ ID NO | Description | Sequence |
|---|---|---|
| 86 | Fc region xELL M252Y and M428L (YL) S354C T366W knob | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVLHEALHNH YTQKSLSLSPGK |
| 87 | Fc region xELL M252Y, M428L, H435R (YLR) S354C T366W knob | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVLHEALHNR YTQKSLSLSPGK |
| 88 | Fc region xELL M252Y, M428V, H435R (YVR) S354C T366W knob | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVVHEALHNR YTQKSLSLSPGK |
| 89 | Fc region xELL T366S, L368A, Y407V hole | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVMHEALHNH YTQKSLSLSPGK |
| 90 | Fc region xELL H435R, T366S, L368A, Y407V hole | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVMHEALHNR YTQKSLSLSPGK |
| 91 | Fc region xELL M252Y and M428V (YV) T366S, L368A, Y407V hole | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVVHEALHNH YTQKSLSLSPGK |
| 92 | Fc region xELL M252Y and M428L (YL) T366S, L368A, Y407V hole | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVLHEALHNH YTQKSLSLSPGK |
| 93 | Fc region xELL M252Y, M428L, H435R (YLR) T366S, L368A, Y407V hole | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVLHEALHNR YTQKSLSLSPGK |
| 94 | Fc region xELL M252Y, M428V, H435R (YVR) T366S, L368A, Y407V hole | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVCTLPPSRDELTKNQVSLSCAVKGFYPSDIAVEWE SNGQPENNYKTTPPVLDSDGSFFLVSKLTVDKSRWQQGNVFSCSVVHEALHNR YTQKSLSLSPGK |
| 95 | Fc region H435R | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNRYTQK SLSLSPGK |

TABLE-continued of Certain Sequences

| SEQ ID NO | Description | Sequence |
|---|---|---|
| 96 | Fc region M252Y and M428V (YV) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNHYTQK SLSLSPGK |
| 97 | Fc region M252Y and M428L (YL) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNHYTQK SLSLSPGK |
| 98 | Fc region M252Y, M428L, H435R (YLR) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNRYTQK SLSLSPGK |
| 99 | Fc region M252Y, M428V, H435R (YVR) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNRYTQK SLSLSPGK |
| 100 | Fc region S354C T366W knob | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNHYTQK SLSLSPGK |
| 101 | Fc region H435R S354C T366W knob | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNRYTQK SLSLSPGK |
| 102 | Fc region M252Y and M428L (YL) S354C T366W knob | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPCRDELTKNQVSLWCLVKGFYPSDIAV EWESNGQPENNYKTTPPVLDSDGSFFLYSKLTVDKSRWQQGNVFSCSVLHEAL HNHYTQKSLSLSPGK |
| 103 | Fc region M252Y, M428L, H435R (YLR) S354C T366W knob | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPCRDELTKNQVSLWCLVKGFYPSDIAV EWESNGQPENNYKTTPPVLDSDGSFFLYSKLTVDKSRWQQGNVFSCSVLHEAL HNRYTQKSLSLSPGK |
| 104 | Fc region M252Y, M428V, H435R (YVR) S354C T366W knob | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPCRDELTKNQVSLWCLVKGFYPSDIAV EWESNGQPENNYKTTPPVLDSDGSFFLYSKLTVDKSRWQQGNVFSCSVVHEAL HNRYTQKSLSLSPGK |
| 105 | Fc region T366S, L368A, Y407V hole | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHEAL HNHYTQKSLSLSPGK |
| 106 | Fc region H435R, T366S, L368A, Y407V hole | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHEAL HNRYTQKSLSLSPGK |

TABLE-continued of Certain Sequences

| SEQ ID NO | Description | Sequence |
|---|---|---|
| 107 | Fc region M252Y and M428V (YV) T366S, L368A, Y407V hole | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVVHEAL HNHYTQKSLSLSPGK |
| 108 | Fc region M252Y and M428L (YL) T366S, L368A, Y407V hole | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVLHEAL HNHYTQKSLSLSPGK |
| 109 | Fc region M252Y, M428L, H435R (YLR) T366S, L368A, Y407V hole | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVLHEAL HNRYTQKSLSLSPGK |
| 110 | CD33 ECD | DPNFWLQVQESVTVQEGLCVLVPCTFFHPIPYYDKNSPVHGYWFREGAIISRD SPVATNKLDQEVQEETQGRFRLLGDPSRNNCSLSIVDARRRDNGSYFFRMERG STKYSYKSPQLSVHVTDLTHRPKILIPGTLEPGHSKNLTCSVSWACEQGTPPI FSWLSAAPTSLGPRTTHSSVLIITPRPQDHGTNLTCQVKFAGAGVTTERTIQL NVTYVPQNPTTGIFPGDGSGKQETRAGVVH |
| 111 | CD33 ECD-AviTag™-His | DPNFWLQVQESVTVQEGLCVLVPCTFFHPIPYYDKNSPVHGYWFREGAIISRD SPVATNKLDQEVQEETQGRFRLLGDPSRNNCSLSIVDARRRDNGSYFFRMERG STKYSYKSPQLSVHVTDLTHRPKILIPGTLEPGHSKNLTCSVSWACEQGTPPI FSWLSAAPTSLGPRTTHSSVLIITPRPQDHGTNLTCQVKFAGAGVTTERTIQL NVTYVPQNPTTGIFPGDGSGKQETRAGVVHGGTGGSGLNDIFEAQKIEWHEHH HHHH |
| 112 | CD33M | DPNFWLQVQESVTVQEGLCVLVPCTFFHPIPYYDKNSPVHGYWFREGAIISRD SPVATNKLDQEVQEETQGRFRLLGDPSRNNCSLSIVDARRRDNGSYFFRMERG STKYSYKSPQLSVHVTDLTHRPKILIPGTLEPGHSKNLTCSVSWACEQGTPPI FSWLSAAPTSLGPRTTHSSVLIITPRPQDHGTNLTCQVKFAGAGVTTERTIQL NVTYVPQNPTTGIFPGDGSGKQETRAGVVHGAIGGAGVTALLALCLCLIFFIV KTHRRKAARTAVGRNDTHPTT |
| 113 | CD33m | DLTHRPKILIPGTLEPGHSKNLTCSVSWACEQGTPPIFSWLSAAPTSLGPRTT HSSVLIITPRPQDHGTNLTCQVKFAGAGVTTERTIQLNVTYVPQNPTTGIFPG DGSGKQETRAGVVH |

What is claimed is:

1. An isolated nucleic acid that encodes a polypeptide comprising at least one VHH domain that binds CD33, wherein at least one VHH domain that binds CD33 comprises:
  a) a CDR1 comprising the amino acid sequence of SEQ ID NO: 47; a CDR2 comprising the amino acid sequence of SEQ ID NO: 48; and a CDR3 comprising the amino acid sequence of SEQ ID NO: 49;
  b) a CDR1 comprising the amino acid sequence of SEQ ID NO: 7; a CDR2 comprising the amino acid sequence of SEQ ID NO: 8; and a CDR3 comprising the amino acid sequence of SEQ ID NO: 9;
  c) a CDR1 comprising the amino acid sequence of SEQ ID NO: 50; a CDR2 comprising the amino acid sequence of SEQ ID NO: 51; and a CDR3 comprising the amino acid sequence of SEQ ID NO: 52;
  d) a CDR1 comprising the amino acid sequence of SEQ ID NO: 56; a CDR2 comprising the amino acid sequence of SEQ ID NO: 54 or 57; and a CDR3 comprising the amino acid sequence of SEQ ID NO: 58;
  e) a CDR1 comprising the amino acid sequence of SEQ ID NO: 59; a CDR2 comprising the amino acid sequence of SEQ ID NO: 60; and a CDR3 comprising the amino acid sequence of SEQ ID NO: 61;
  f) a CDR1 comprising the amino acid sequence of SEQ ID NO: 23 or 62; a CDR2 comprising the amino acid sequence of SEQ ID NO: 63; and a CDR3 comprising the amino acid sequence of SEQ ID NO: 64;
  g) a CDR1 comprising the amino acid sequence of SEQ ID NO: 65; a CDR2 comprising the amino acid sequence of SEQ ID NO: 66; and a CDR3 comprising the amino acid sequence of SEQ ID NO: 67;
  h) a CDR1 comprising the amino acid sequence of SEQ ID NO: 68; a CDR2 comprising the amino acid sequence of SEQ ID NO: 69; and a CDR3 comprising the amino acid sequence of SEQ ID NO: 70; or
  i) a CDR1 comprising the amino acid sequence of SEQ ID NO: 71; a CDR2 comprising the amino acid sequence of SEQ ID NO: 72; and a CDR3 comprising the amino acid sequence of SEQ ID NO: 73.

2. The isolated nucleic acid of claim 1, wherein at least one VHH domain comprises a CDR1 comprising the amino acid sequence of SEQ ID NO: 47; a CDR2 comprising the amino acid sequence of SEQ ID NO: 48; and a CDR3 comprising the amino acid sequence of SEQ ID NO: 49.

3. The isolated nucleic acid of claim 1, wherein at least one VHH domain comprises a CDR1 comprising the amino acid sequence of SEQ ID NO: 7; a CDR2 comprising the amino acid sequence of SEQ ID NO: 8; and a CDR3 comprising the amino acid sequence of SEQ ID NO: 9.

4. The isolated nucleic acid of claim 1, wherein at least one VHH domain comprises a CDR1 comprising the amino acid sequence of SEQ ID NO: 50; a CDR2 comprising the amino acid sequence of SEQ ID NO: 51; and a CDR3 comprising the amino acid sequence of SEQ ID NO: 52.

5. The isolated nucleic acid of claim 1, wherein at least one VHH domain comprises a CDR1 comprising the amino acid sequence of SEQ ID NO: 56; a CDR2 comprising the amino acid sequence of SEQ ID NO: 54 or 57; and a CDR3 comprising the amino acid sequence of SEQ ID NO: 58.

6. The isolated nucleic acid of claim 1, wherein at least one VHH domain comprises a CDR1 comprising the amino acid sequence of SEQ ID NO: 59; a CDR2 comprising the amino acid sequence of SEQ ID NO: 60; and a CDR3 comprising the amino acid sequence of SEQ ID NO: 61.

7. The isolated nucleic acid of claim 1, wherein at least one VHH domain comprises a CDR1 comprising the amino acid sequence of SEQ ID NO: 23 or 62; a CDR2 comprising the amino acid sequence of SEQ ID NO: 63; and a CDR3 comprising the amino acid sequence of SEQ ID NO: 64.

8. The isolated nucleic acid of claim 1, wherein at least one VHH domain comprises a CDR1 comprising the amino acid sequence of SEQ ID NO: 65; a CDR2 comprising the amino acid sequence of SEQ ID NO: 66; and a CDR3 comprising the amino acid sequence of SEQ ID NO: 67.

9. The isolated nucleic acid of claim 1, wherein at least one VHH domain comprises a CDR1 comprising the amino acid sequence of SEQ ID NO: 68; a CDR2 comprising the amino acid sequence of SEQ ID NO: 69; and a CDR3 comprising the amino acid sequence of SEQ ID NO: 70.

10. The isolated nucleic acid of claim 1, wherein at least one VHH domain comprises a CDR1 comprising the amino acid sequence of SEQ ID NO: 71; a CDR2 comprising the amino acid sequence of SEQ ID NO: 72; and a CDR3 comprising the amino acid sequence of SEQ ID NO: 73.

11. The isolated nucleic acid of claim 1, wherein at least one VHH domain is humanized.

12. The isolated nucleic acid of claim 1, wherein at least one VHH domain comprises an amino acid sequence at least 90% identical to the amino acid sequence of SEQ ID NO: 38, 114, 39, 40, 41, 42, 43, 44, 45, 46, 115, 116, 117, 118, 119, 120, 121, or 122.

13. The isolated nucleic acid of claim 1, wherein at least one VHH domain comprises the amino acid sequence of SEQ ID NO: 38, 114, 39, 40, 41, 42, 43, 44, 45, 46, 115, 116, 117, 118, 119, 120, 121, or 122.

14. The isolated nucleic acid of claim 1, wherein at least one VHH domain comprises the amino acid sequence of SEQ ID NO: 38 or 114.

15. The isolated nucleic acid of claim 1, wherein at least one VHH domain comprises an amino acid sequence at least 90% identical to the amino acid sequence of SEQ ID NO: 2, 6, 10, 14, 18, 22, 26, 30, 34, 123, 124, 125, 126, 127, 128, 129, 130, or 131.

16. The isolated nucleic acid of claim 1, wherein the polypeptide comprises one, two, or three VHH domains.

17. The isolated nucleic acid of claim 1, wherein the polypeptide comprises at least one binding domain that binds an antigen other than CD33.

18. The nucleic acid of claim 17, wherein at least one VHH domain comprises the amino acid sequence of SEQ ID NO: 38 or 114.

19. The isolated nucleic acid of claim 17, wherein the polypeptide comprises at least one binding domain that binds CD3, T-cell receptor (TCR) α, TCRβ, CD28, CD16, CD32A, CD64, CD89, NKp46, or NKG2D.

20. The isolated nucleic acid of claim 16, wherein each VHH domain binds CD33.

21. The nucleic acid of claim 20, wherein at least one VHH domain comprises the amino acid sequence of SEQ ID NO: 38 or 114.

22. The isolated nucleic acid of claim 1, wherein the polypeptide comprises an Fc region.

23. The isolated nucleic acid of claim 22, wherein the Fc region comprises an amino acid sequence selected from SEQ ID NOs: 74-109.

24. A vector comprising the isolated nucleic acid of claim 1.

25. A host cell comprising the isolated nucleic acid of claim 1.

26. The host cell of claim 25, wherein at least one VHH domain comprises the amino acid sequence of SEQ ID NO: 38 or 114.

27. A method of producing a polypeptide, comprising incubating the host cell of claim 25 under conditions suitable for expression of the polypeptide, and isolating the polypeptide.

* * * * *

SEQUENCE LISTING

```
Sequence total quantity: 131
SEQ ID NO: 1              moltype = AA  length = 347
FEATURE                   Location/Qualifiers
source                    1..347
                          mol_type = protein
                          organism = Homo sapiens
SEQUENCE: 1
DPNFWLQVQE SVTVQEGLCV LVPCTFFHPI PYYDKNSPVH GYWFREGAII SRDSPVATNK  60
LDQEVQEETQ GRFRLLGDPS RNNCSLSIVD ARRRDNGSYF FRMERGSTKY SYKSPQLSVH 120
VTDLTHRPKI LIPGTLEPGH SKNLTCSVSW ACEQGTPPIF SWLSAAPTSL GPRTTHSSVL 180
IITPRPQDHG TNLTCQVKFA GAGVTTERTI QLNVTYVPQN PTTGIFPGDG SGKQETRAGV 240
VHGAIGGAGV TALLALCLCL IFFIVKTHRR KAARTAVGRN DTHPTTGSAS PKHQKKSKLH 300
GPTETSSCSG AAPTVEMDEE LHYASLNFHG MNPSKDTSTE YSEVRTQ              347

SEQ ID NO: 2              moltype = AA  length = 114
FEATURE                   Location/Qualifiers
REGION                    1..114
                          note = A07
source                    1..114
                          mol_type = protein
                          organism = synthetic construct
```

```
SEQUENCE: 2
QVQLVQSGGG LVQAGGSLTL SCAASRSSGI DVMGWYRQAP GKERELVAEI SGVGDTNYAA    60
SLADRFTVSR DNAKNTVYLQ MKNLKPEDTA VYYCNAHSFL DLVGAWGQGT QVTV         114

SEQ ID NO: 3            moltype = AA   length = 9
FEATURE                 Location/Qualifiers
REGION                  1..9
                        note = A07 CDR1
source                  1..9
                        mol_type = protein
                        organism = synthetic construct
SEQUENCE: 3
RSSGIDVMG                                                              9

SEQ ID NO: 4            moltype = AA   length = 9
FEATURE                 Location/Qualifiers
REGION                  1..9
                        note = A07 CDR2
source                  1..9
                        mol_type = protein
                        organism = synthetic construct
SEQUENCE: 4
EISGVGDTN                                                              9

SEQ ID NO: 5            moltype = AA   length = 9
FEATURE                 Location/Qualifiers
REGION                  1..9
                        note = A07 CDR3
source                  1..9
                        mol_type = protein
                        organism = synthetic construct
SEQUENCE: 5
HSFLDLVGA                                                              9

SEQ ID NO: 6            moltype = AA   length = 115
FEATURE                 Location/Qualifiers
REGION                  1..115
                        note = 401-A9
source                  1..115
                        mol_type = protein
                        organism = synthetic construct
SEQUENCE: 6
QVQLQQSGGG LVQAGGSLRL SCAAPGSINS INVMEWYRQA PGKERDLVAG ITSDGDTNYV    60
DSVPGRFTIT RDNTMRTVDL QMNNLKADDT AVYYCRARDW GSLTDYWGQG TQVTV         115

SEQ ID NO: 7            moltype = AA   length = 10
FEATURE                 Location/Qualifiers
REGION                  1..10
                        note = 401-A9 CDR1
source                  1..10
                        mol_type = protein
                        organism = synthetic construct
SEQUENCE: 7
GSINSINVME                                                            10

SEQ ID NO: 8            moltype = AA   length = 9
FEATURE                 Location/Qualifiers
REGION                  1..9
                        note = 401-A9 CDR2
source                  1..9
                        mol_type = protein
                        organism = synthetic construct
SEQUENCE: 8
GITSDGDTN                                                              9

SEQ ID NO: 9            moltype = AA   length = 9
FEATURE                 Location/Qualifiers
REGION                  1..9
                        note = 401-A9 CDR3
source                  1..9
                        mol_type = protein
                        organism = synthetic construct
SEQUENCE: 9
RDWGSLTDY                                                              9

SEQ ID NO: 10           moltype = AA   length = 122
FEATURE                 Location/Qualifiers
REGION                  1..122
                        note = B07
```

```
source                  1..122
                        mol_type = protein
                        organism = synthetic construct
SEQUENCE: 10
EVQLVQSGGG LVQTGGSLRL SCGASGRTIS DYVVGWFRQA PGKERAFVAA ISRYGTTYYA    60
ASVQGRFTIS RDNPRNTVYL QVDSLRPEDT AVYFCAALQN DVRNNHSPTS YDYWGQGTQV   120
TV                                                                 122

SEQ ID NO: 11           moltype = AA  length = 10
FEATURE                 Location/Qualifiers
REGION                  1..10
                        note = B07 CDR1
source                  1..10
                        mol_type = protein
                        organism = synthetic construct
SEQUENCE: 11
GRTISDYVVG                                                          10

SEQ ID NO: 12           moltype = AA  length = 9
FEATURE                 Location/Qualifiers
REGION                  1..9
                        note = B07 CDR2
source                  1..9
                        mol_type = protein
                        organism = synthetic construct
SEQUENCE: 12
AISRYGTTY                                                            9

SEQ ID NO: 13           moltype = AA  length = 16
FEATURE                 Location/Qualifiers
REGION                  1..16
                        note = B07 CDR3
source                  1..16
                        mol_type = protein
                        organism = synthetic construct
SEQUENCE: 13
LQNDVRNNHS PTSYDY                                                   16

SEQ ID NO: 14           moltype = AA  length = 118
FEATURE                 Location/Qualifiers
REGION                  1..118
                        note = 1C7
source                  1..118
                        mol_type = protein
                        organism = synthetic construct
SEQUENCE: 14
QVQLQQSGGG LVQAGGSLRL SCAASGRTFS GYIMGWFRQV PGKERELVAR ISGNNLSTEY    60
GGSVKGRFTI SRDSAKETMY LQMNSLKPED TAIYYCAAEY DYSSGDFVYW GQGTQVTV    118

SEQ ID NO: 15           moltype = AA  length = 10
FEATURE                 Location/Qualifiers
REGION                  1..10
                        note = 1C7 CDR1
source                  1..10
                        mol_type = protein
                        organism = synthetic construct
SEQUENCE: 15
GRTFSGYIMG                                                          10

SEQ ID NO: 16           moltype = AA  length = 10
FEATURE                 Location/Qualifiers
REGION                  1..10
                        note = 1C7 CDR2
source                  1..10
                        mol_type = protein
                        organism = synthetic construct
SEQUENCE: 16
RISGNNLSTE                                                          10

SEQ ID NO: 17           moltype = AA  length = 11
FEATURE                 Location/Qualifiers
REGION                  1..11
                        note = 1C7 CDR3
source                  1..11
                        mol_type = protein
                        organism = synthetic construct
SEQUENCE: 17
EYDYSSGDFV Y                                                        11
```

```
SEQ ID NO: 18              moltype = AA  length = 116
FEATURE                    Location/Qualifiers
REGION                     1..116
                           note = 1E4
source                     1..116
                           mol_type = protein
                           organism = synthetic construct
SEQUENCE: 18
QVQLQQSGGG SVQAGGSLRL SCVASGSGFS ASLMSWHRQA PGSQRDLVAS ITRDGRANYV   60
DSVKDRFTIS RDNAKNTAYL QMDSLKPEDT AAYYCHAYSF DYPIRSYWGQ GTQVTV      116

SEQ ID NO: 19              moltype = AA  length = 10
FEATURE                    Location/Qualifiers
REGION                     1..10
                           note = 1E4 CDR1
source                     1..10
                           mol_type = protein
                           organism = synthetic construct
SEQUENCE: 19
GSGFSASLMS                                                         10

SEQ ID NO: 20              moltype = AA  length = 9
FEATURE                    Location/Qualifiers
REGION                     1..9
                           note = 1E4 CDR2
source                     1..9
                           mol_type = protein
                           organism = synthetic construct
SEQUENCE: 20
SITRDGRAN                                                          9

SEQ ID NO: 21              moltype = AA  length = 10
FEATURE                    Location/Qualifiers
REGION                     1..10
                           note = 1E4 CDR3
source                     1..10
                           mol_type = protein
                           organism = synthetic construct
SEQUENCE: 21
YSFDYPIRSY                                                         10

SEQ ID NO: 22              moltype = AA  length = 122
FEATURE                    Location/Qualifiers
REGION                     1..122
                           note = F02
source                     1..122
                           mol_type = protein
                           organism = synthetic construct
SEQUENCE: 22
QVQLVQSGGG LVQAGGSLRL SCAASGSISS YNVVGWYRQL SGNERGGRTM VAQINAYGDT   60
NYANAVVGRF TISRDDAKNT VYLHMSNLKP EDTGVYYCNG QRMLENYTYR DQSWGQGTQV   120
TV                                                                 122

SEQ ID NO: 23              moltype = AA  length = 10
FEATURE                    Location/Qualifiers
REGION                     1..10
                           note = F02 CDR1
source                     1..10
                           mol_type = protein
                           organism = synthetic construct
SEQUENCE: 23
GSISSYNVVG                                                         10

SEQ ID NO: 24              moltype = AA  length = 9
FEATURE                    Location/Qualifiers
REGION                     1..9
                           note = F02 CDR2
source                     1..9
                           mol_type = protein
                           organism = synthetic construct
SEQUENCE: 24
QINAYGDTN                                                          9

SEQ ID NO: 25              moltype = AA  length = 13
FEATURE                    Location/Qualifiers
REGION                     1..13
                           note = F02 CDR3
source                     1..13
                           mol_type = protein
```

```
                                             organism = synthetic construct
SEQUENCE: 25
QRMLENYTYR DQS                                                                          13

SEQ ID NO: 26            moltype = AA  length = 116
FEATURE                  Location/Qualifiers
REGION                   1..116
                         note = 1G3
source                   1..116
                         mol_type = protein
                         organism = synthetic construct
SEQUENCE: 26
EVQLQQSGGG EVQPGGSLRL SCEASGFTFS SYAMGWFRQA PGKGREWVAA ITTSGDTTYY         60
AESVKGRFTI SRDNAKNTVY LQMSSLRAED TAVYYCAAHR GGGVIDYWGQ GTQVTV            116

SEQ ID NO: 27            moltype = AA  length = 10
FEATURE                  Location/Qualifiers
REGION                   1..10
                         note = 1G3 CDR1
source                   1..10
                         mol_type = protein
                         organism = synthetic construct
SEQUENCE: 27
GFTFSSYAMG                                                                              10

SEQ ID NO: 28            moltype = AA  length = 10
FEATURE                  Location/Qualifiers
REGION                   1..10
                         note = 1G3 CDR2
source                   1..10
                         mol_type = protein
                         organism = synthetic construct
SEQUENCE: 28
AITTSGDTTY                                                                              10

SEQ ID NO: 29            moltype = AA  length = 9
FEATURE                  Location/Qualifiers
REGION                   1..9
                         note = 1G3 CDR3
source                   1..9
                         mol_type = protein
                         organism = synthetic construct
SEQUENCE: 29
HRGGGVIDY                                                                                9

SEQ ID NO: 30            moltype = AA  length = 118
FEATURE                  Location/Qualifiers
REGION                   1..118
                         note = G11
source                   1..118
                         mol_type = protein
                         organism = synthetic construct
SEQUENCE: 30
EVQLVQSGGG SVQVGGSLRL SCAASGSTLN IDHIGWYRQA PGKERELVGV ISSGAGPNYA         60
DSVKGRFTIS RDNAKNTVYL QMNSLKPEDT AVYNCNAWID YGSGLPQNYW GQGTQVTV         118

SEQ ID NO: 31            moltype = AA  length = 10
FEATURE                  Location/Qualifiers
REGION                   1..10
                         note = G11 CDR1
source                   1..10
                         mol_type = protein
                         organism = synthetic construct
SEQUENCE: 31
GSTLNIDHIG                                                                              10

SEQ ID NO: 32            moltype = AA  length = 9
FEATURE                  Location/Qualifiers
REGION                   1..9
                         note = G11 CDR2
source                   1..9
                         mol_type = protein
                         organism = synthetic construct
SEQUENCE: 32
VISSGAGPN                                                                                9

SEQ ID NO: 33            moltype = AA  length = 12
FEATURE                  Location/Qualifiers
REGION                   1..12
```

```
                           note = G11 CDR3
source                     1..12
                           mol_type = protein
                           organism = synthetic construct
SEQUENCE: 33
WIDYGSGLPQ NY                                                              12

SEQ ID NO: 34              moltype = AA  length = 119
FEATURE                    Location/Qualifiers
REGION                     1..119
                           note = 1H9
source                     1..119
                           mol_type = protein
                           organism = synthetic construct
SEQUENCE: 34
EVQLQQSGGA VVQPGGSLRL SCAASGSIFS ISIMGWYRQA PGKERELVAS TTSSGTTNYV           60
DSVKGRFTAS RDNAKNTVYL QMNSLKPDDT AIYHCHAYIA TTTDRGYRGY WGQGTQVTV           119

SEQ ID NO: 35              moltype = AA  length = 10
FEATURE                    Location/Qualifiers
REGION                     1..10
                           note = 1H9 CDR1
source                     1..10
                           mol_type = protein
                           organism = synthetic construct
SEQUENCE: 35
GSIFSISIMG                                                                 10

SEQ ID NO: 36              moltype = AA  length = 9
FEATURE                    Location/Qualifiers
REGION                     1..9
                           note = 1H9 CDR2
source                     1..9
                           mol_type = protein
                           organism = synthetic construct
SEQUENCE: 36
STTSSGTTN                                                                  9

SEQ ID NO: 37              moltype = AA  length = 13
FEATURE                    Location/Qualifiers
REGION                     1..13
                           note = 1H9 CDR3
source                     1..13
                           mol_type = protein
                           organism = synthetic construct
SEQUENCE: 37
YIATTTDRGY RGY                                                             13

SEQ ID NO: 38              moltype = AA  length = 114
FEATURE                    Location/Qualifiers
REGION                     1..114
                           note = hzA07v4
source                     1..114
                           mol_type = protein
                           organism = synthetic construct
SEQUENCE: 38
EVQLVESGGG EVQPGGSLRL SCAASRSSGI DVMGWYRQAP GKERELVAEI SGVGDTNYAA           60
SLADRFTVSR DNAKNTVYLQ MSSLRAEDTA VYYCNAHSFL DLVGAWGQGT LVTV                114

SEQ ID NO: 39              moltype = AA  length = 122
FEATURE                    Location/Qualifiers
REGION                     1..122
                           note = hzB07v7
source                     1..122
                           mol_type = protein
                           organism = synthetic construct
SEQUENCE: 39
EVQLVESGGG EVQPGGSLRL SCAASGRTIS DYVVGWFRQA PGKERAFVAA ISRYGTTYYA           60
ASVQGRFTIS RDNPRNTVYL QVDSLRAEDT AVYYCAALQN DVRNNHSPTS YDYWGQGTLV          120
TV                                                                        122

SEQ ID NO: 40              moltype = AA  length = 118
FEATURE                    Location/Qualifiers
REGION                     1..118
                           note = hz1C7v1
source                     1..118
                           mol_type = protein
                           organism = synthetic construct
SEQUENCE: 40
```

```
EVQLVESGGG EVQPGGSLRL SCAASGRTFS GYIMGWFRQA PGKERELVAR ISGNNLSTEY    60
AESVKGRFTI SRDNAKNTLY LQMSSLRAED TAVYYCAAEY DYSSGDFVYW GQGTLVTV    118

SEQ ID NO: 41           moltype = AA  length = 118
FEATURE                 Location/Qualifiers
REGION                  1..118
                        note = hz1C7v11
source                  1..118
                        mol_type = protein
                        organism = synthetic construct
SEQUENCE: 41
EVQLVESGGG EVQPGGSLRL SCAASGRTFS GYIMGWFRQA PGKERELVAR ISGNNLATEY    60
AESVKGRFTI SRDNAKNTLY LQMSSLRAED TAVYYCAAEY DYSSGDFVYW GQGTLVTV    118

SEQ ID NO: 42           moltype = AA  length = 116
FEATURE                 Location/Qualifiers
REGION                  1..116
                        note = hz1E4v2
source                  1..116
                        mol_type = protein
                        organism = synthetic construct
SEQUENCE: 42
EVQLVESGGG EVQPGGSLRL SCAASGSGFS ASLMSWHRQA PGKQRDLVAS ITRDGRANYV    60
ESVKGRFTIS RDNAKNTLYL QMSSLRAEDT AVYYCHAYSF DYPIRSYWGQ GTLVTV      116

SEQ ID NO: 43           moltype = AA  length = 119
FEATURE                 Location/Qualifiers
REGION                  1..119
                        note = hzF02v18
source                  1..119
                        mol_type = protein
                        organism = synthetic construct
SEQUENCE: 43
EVQLVESGGG EVQPGGSLRL SCAASGSISS YNVMGWYRQA PGKQRELVAQ INAYGDTNYA    60
NAVVGRFTIS RDNAKNTVYL QMSSLRAEDT AVYYCNGQRM LENYTYRDQS WGQGTLVTV   119

SEQ ID NO: 44           moltype = AA  length = 116
FEATURE                 Location/Qualifiers
REGION                  1..116
                        note = hz1G3v3
source                  1..116
                        mol_type = protein
                        organism = synthetic construct
SEQUENCE: 44
EVQLVESGGG EVQPGGSLRL SCAASGFTFS SYAMGWFRQA PGKGREWVAA ITTSGDTTYY    60
AESVKGRFTI SRDNAKNTVY LQMSSLRAED TAVYYCAAHR GGGVIDYWGQ GTLVTV      116

SEQ ID NO: 45           moltype = AA  length = 118
FEATURE                 Location/Qualifiers
REGION                  1..118
                        note = hzG11v2
source                  1..118
                        mol_type = protein
                        organism = synthetic construct
SEQUENCE: 45
EVQLVESGGG EVQPGGSLRL SCAASGSTLN IDHIGWYRQA PGKERELVGV ISSGAGPNYA    60
ESVKGRFTIS RDNAKNTVYL QMSSLRAEDT AVYYCNAWID YGSGLPQNYW GQGTLVTV    118

SEQ ID NO: 46           moltype = AA  length = 119
FEATURE                 Location/Qualifiers
REGION                  1..119
                        note = hz1H9v2
source                  1..119
                        mol_type = protein
                        organism = synthetic construct
SEQUENCE: 46
EVQLVESGGG EVQPGGSLRL SCAASGSIFS ISIMGWYRQA PGKERELVAS TTSSGTTNYV    60
ESVKGRFTIS RDNAKNTLYL QMSSLRAEDT AVYYCHAYIA TTTDRGYRGY WGQGTLVTV   119

SEQ ID NO: 47           moltype = AA  length = 9
FEATURE                 Location/Qualifiers
REGION                  1..9
                        note = CDR1 or hzA07v4
source                  1..9
                        mol_type = protein
                        organism = synthetic construct
SEQUENCE: 47
RSSGIDVMG                                                            9
```

```
SEQ ID NO: 48              moltype = AA  length = 9
FEATURE                    Location/Qualifiers
REGION                     1..9
                           note = CDR2 of hzA07v4
source                     1..9
                           mol_type = protein
                           organism = synthetic construct
SEQUENCE: 48
EISGVGDTN                                                                     9

SEQ ID NO: 49              moltype = AA  length = 9
FEATURE                    Location/Qualifiers
REGION                     1..9
                           note = CDR3 of hzA07v4
source                     1..9
                           mol_type = protein
                           organism = synthetic construct
SEQUENCE: 49
HSFLDLVGA                                                                     9

SEQ ID NO: 50              moltype = AA  length = 10
FEATURE                    Location/Qualifiers
REGION                     1..10
                           note = CDR1 or hzB07v7
source                     1..10
                           mol_type = protein
                           organism = synthetic construct
SEQUENCE: 50
GRTISDYVVG                                                                   10

SEQ ID NO: 51              moltype = AA  length = 9
FEATURE                    Location/Qualifiers
REGION                     1..9
                           note = CDR2 of hzB07v7
source                     1..9
                           mol_type = protein
                           organism = synthetic construct
SEQUENCE: 51
AISRYGTTY                                                                     9

SEQ ID NO: 52              moltype = AA  length = 16
FEATURE                    Location/Qualifiers
REGION                     1..16
                           note = CDR3 of hzB07v7
source                     1..16
                           mol_type = protein
                           organism = synthetic construct
SEQUENCE: 52
LQNDVRNNHS PTSYDY                                                            16

SEQ ID NO: 53              moltype = AA  length = 10
FEATURE                    Location/Qualifiers
REGION                     1..10
                           note = CDR1 of hz1C7v1
source                     1..10
                           mol_type = protein
                           organism = synthetic construct
SEQUENCE: 53
GRTFSGYIMG                                                                   10

SEQ ID NO: 54              moltype = AA  length = 10
FEATURE                    Location/Qualifiers
REGION                     1..10
                           note = CDR2 of hz1C7v1
source                     1..10
                           mol_type = protein
                           organism = synthetic construct
SEQUENCE: 54
RISGNNLSTE                                                                   10

SEQ ID NO: 55              moltype = AA  length = 11
FEATURE                    Location/Qualifiers
REGION                     1..11
                           note = CDR3 of hz1C7v1
source                     1..11
                           mol_type = protein
                           organism = synthetic construct
SEQUENCE: 55
EYDYSSGDFV Y                                                                 11
```

```
SEQ ID NO: 56            moltype = AA   length = 10
FEATURE                  Location/Qualifiers
REGION                   1..10
                         note = CDR1 of hz1C7v11
source                   1..10
                         mol_type = protein
                         organism = synthetic construct
SEQUENCE: 56
GRTFSGYIMG                                                                10

SEQ ID NO: 57            moltype = AA   length = 10
FEATURE                  Location/Qualifiers
REGION                   1..10
                         note = CDR2 of hz1C7v11
source                   1..10
                         mol_type = protein
                         organism = synthetic construct
SEQUENCE: 57
RISGNNLATE                                                                10

SEQ ID NO: 58            moltype = AA   length = 11
FEATURE                  Location/Qualifiers
REGION                   1..11
                         note = CDR3 of hz1C7v11
source                   1..11
                         mol_type = protein
                         organism = synthetic construct
SEQUENCE: 58
EYDYSSGDFV Y                                                              11

SEQ ID NO: 59            moltype = AA   length = 10
FEATURE                  Location/Qualifiers
REGION                   1..10
                         note = CDR1 of hz1E4v2
source                   1..10
                         mol_type = protein
                         organism = synthetic construct
SEQUENCE: 59
GSGFSASLMS                                                                10

SEQ ID NO: 60            moltype = AA   length = 9
FEATURE                  Location/Qualifiers
REGION                   1..9
                         note = CDR2 of hz1E4v2
source                   1..9
                         mol_type = protein
                         organism = synthetic construct
SEQUENCE: 60
SITRDGRAN                                                                  9

SEQ ID NO: 61            moltype = AA   length = 10
FEATURE                  Location/Qualifiers
REGION                   1..10
                         note = CDR3 of hz1E4v2
source                   1..10
                         mol_type = protein
                         organism = synthetic construct
SEQUENCE: 61
YSFDYPIRSY                                                                10

SEQ ID NO: 62            moltype = AA   length = 10
FEATURE                  Location/Qualifiers
REGION                   1..10
                         note = CDR1 of hzF02v18
source                   1..10
                         mol_type = protein
                         organism = synthetic construct
SEQUENCE: 62
GSISSYNVMG                                                                10

SEQ ID NO: 63            moltype = AA   length = 9
FEATURE                  Location/Qualifiers
REGION                   1..9
                         note = CDR2 of hzF02v18
source                   1..9
                         mol_type = protein
                         organism = synthetic construct
SEQUENCE: 63
```

-continued

```
QINAYGDTN                                                                            9

SEQ ID NO: 64           moltype = AA  length = 13
FEATURE                 Location/Qualifiers
REGION                  1..13
                        note = CDR3 of hzF02v18
source                  1..13
                        mol_type = protein
                        organism = synthetic construct
SEQUENCE: 64
QRMLENYTYR DQS                                                                      13

SEQ ID NO: 65           moltype = AA  length = 10
FEATURE                 Location/Qualifiers
REGION                  1..10
                        note = CDR1 of hz1G3v3
source                  1..10
                        mol_type = protein
                        organism = synthetic construct
SEQUENCE: 65
GFTFSSYAMG                                                                          10

SEQ ID NO: 66           moltype = AA  length = 10
FEATURE                 Location/Qualifiers
REGION                  1..10
                        note = CDR2 of hz1G3v3
source                  1..10
                        mol_type = protein
                        organism = synthetic construct
SEQUENCE: 66
AITTSGDTTY                                                                          10

SEQ ID NO: 67           moltype = AA  length = 9
FEATURE                 Location/Qualifiers
REGION                  1..9
                        note = CDR3 of hz1G3v3
source                  1..9
                        mol_type = protein
                        organism = synthetic construct
SEQUENCE: 67
HRGGGVIDY                                                                            9

SEQ ID NO: 68           moltype = AA  length = 10
FEATURE                 Location/Qualifiers
REGION                  1..10
                        note = CDR1 of hzG11v2
source                  1..10
                        mol_type = protein
                        organism = synthetic construct
SEQUENCE: 68
GSTLNIDHIG                                                                          10

SEQ ID NO: 69           moltype = AA  length = 9
FEATURE                 Location/Qualifiers
REGION                  1..9
                        note = CDR2 of hzG11v2
source                  1..9
                        mol_type = protein
                        organism = synthetic construct
SEQUENCE: 69
VISSGAGPN                                                                            9

SEQ ID NO: 70           moltype = AA  length = 12
FEATURE                 Location/Qualifiers
REGION                  1..12
                        note = CDR3 of hzG11v2
source                  1..12
                        mol_type = protein
                        organism = synthetic construct
SEQUENCE: 70
WIDYGSGLPQ NY                                                                       12

SEQ ID NO: 71           moltype = AA  length = 10
FEATURE                 Location/Qualifiers
REGION                  1..10
                        note = CDR1 of hz1H9v2
source                  1..10
                        mol_type = protein
                        organism = synthetic construct
```

```
SEQUENCE: 71
GSIFSISIMG                                                                              10

SEQ ID NO: 72              moltype = AA  length = 9
FEATURE                    Location/Qualifiers
REGION                     1..9
                           note = CDR2 of hz1H9v2
source                     1..9
                           mol_type = protein
                           organism = synthetic construct
SEQUENCE: 72
STTSSGTTN                                                                                9

SEQ ID NO: 73              moltype = AA  length = 13
FEATURE                    Location/Qualifiers
REGION                     1..13
                           note = CDR3 of hz1H9v2
source                     1..13
                           mol_type = protein
                           organism = synthetic construct
SEQUENCE: 73
YIATTTDRGY RGY                                                                          13

SEQ ID NO: 74              moltype = AA  length = 227
FEATURE                    Location/Qualifiers
source                     1..227
                           mol_type = protein
                           organism = Homo sapiens
SEQUENCE: 74
DKTHTCPPCP APELLGGPSV FLFPPKPKDT LMISRTPEVT CVVVDVSHED PEVKFNWYVD                         60
GVEVHNAKTK PREEQYNSTY RVVSVLTVLH QDWLNGKEYK CKVSNKALPA PIEKTISKAK                        120
GQPREPQVYT LPPSRDELTK NQVSLTCLVK GFYPSDIAVE WESNGQPENN YKTTPPVLDS                        180
DGSFFLYSKL TVDKSRWQQG NVFSCSVMHE ALHNHYTQKS LSLSPGK                                     227

SEQ ID NO: 75              moltype = AA  length = 224
FEATURE                    Location/Qualifiers
REGION                     1..224
                           note = human IgG1 xELL Fc region
source                     1..224
                           mol_type = protein
                           organism = synthetic construct
SEQUENCE: 75
DKTHTCPPCP APGGPSVFLF PPKPKDTLMI SRTPEVTCVV VDVSHEDPEV KFNWYVDGVE                         60
VHNAKTKPRE EQYNSTYRVV SVLTVLHQDW LNGKEYKCKV SNKALPAPIE KTISKAKGQP                        120
REPQVYTLPP SRDELTKNQV SLTCLVKGFY PSDIAVEWES NGQPENNYKT TPPVLDSDGS                        180
FFLYSKLTVD KSRWQQGNVF SCSVMHEALH NHYTQKSLSL SPGK                                        224

SEQ ID NO: 76              moltype = AA  length = 227
FEATURE                    Location/Qualifiers
REGION                     1..227
                           note = Fc region M252Y and M428V (YV) S354C T366W knob
source                     1..227
                           mol_type = protein
                           organism = synthetic construct
SEQUENCE: 76
DKTHTCPPCP APELLGGPSV FLFPPKPKDT LYISRTPEVT CVVVDVSHED PEVKFNWYVD                         60
GVEVHNAKTK PREEQYNSTY RVVSVLTVLH QDWLNGKEYK CKVSNKALPA PIEKTISKAK                        120
GQPREPQVYT LPPCRDELTK NQVSLWCLVK GFYPSDIAVE WESNGQPENN YKTTPPVLDS                        180
DGSFFLYSKL TVDKSRWQQG NVFSCSVVHE ALHNHYTQKS LSLSPGK                                     227

SEQ ID NO: 77              moltype = AA  length = 227
FEATURE                    Location/Qualifiers
REGION                     1..227
                           note = Fc region M252Y, M428V, H435R (YVR) T366S, L368A,
                           Y407V hole
source                     1..227
                           mol_type = protein
                           organism = synthetic construct
SEQUENCE: 77
DKTHTCPPCP APELLGGPSV FLFPPKPKDT LYISRTPEVT CVVVDVSHED PEVKFNWYVD                         60
GVEVHNAKTK PREEQYNSTY RVVSVLTVLH QDWLNGKEYK CKVSNKALPA PIEKTISKAK                        120
GQPREPQVCT LPPSRDELTK NQVSLSCAVK GFYPSDIAVE WESNGQPENN YKTTPPVLDS                        180
DGSFFLVSKL TVDKSRWQQG NVFSCSVVHE ALHNRYTQKS LSLSPGK                                     227

SEQ ID NO: 78              moltype = AA  length = 224
FEATURE                    Location/Qualifiers
REGION                     1..224
                           note = Fc region xELL H435R
source                     1..224
```

```
                              mol_type = protein
                              organism = synthetic construct
SEQUENCE: 78
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVMHEALH NRYTQKSLSL SPGK                    224

SEQ ID NO: 79                 moltype = AA  length = 224
FEATURE                       Location/Qualifiers
REGION                        1..224
                              note = Fc region xELL M252Y and M428V (YV)
source                        1..224
                              mol_type = protein
                              organism = synthetic construct
SEQUENCE: 79
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVVHEALH NHYTQKSLSL SPGK                    224

SEQ ID NO: 80                 moltype = AA  length = 224
FEATURE                       Location/Qualifiers
REGION                        1..224
                              note = Fc region xELL M252Y and M428L (YL)
source                        1..224
                              mol_type = protein
                              organism = synthetic construct
SEQUENCE: 80
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVLHEALH NHYTQKSLSL SPGK                    224

SEQ ID NO: 81                 moltype = AA  length = 224
FEATURE                       Location/Qualifiers
REGION                        1..224
                              note = Fc region xELL M252Y, M428L, H435R (YLR)
source                        1..224
                              mol_type = protein
                              organism = synthetic construct
SEQUENCE: 81
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVLHEALH NRYTQKSLSL SPGK                    224

SEQ ID NO: 82                 moltype = AA  length = 224
FEATURE                       Location/Qualifiers
REGION                        1..224
                              note = Fc region xELL M252Y, M428V, H435R (YVR)
source                        1..224
                              mol_type = protein
                              organism = synthetic construct
SEQUENCE: 82
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVVHEALH NRYTQKSLSL SPGK                    224

SEQ ID NO: 83                 moltype = AA  length = 224
FEATURE                       Location/Qualifiers
REGION                        1..224
                              note = Fc region xELL S354C T366W knob
source                        1..224
                              mol_type = protein
                              organism = synthetic construct
SEQUENCE: 83
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVMHEALH NHYTQKSLSL SPGK                    224

SEQ ID NO: 84                 moltype = AA  length = 224
FEATURE                       Location/Qualifiers
REGION                        1..224
                              note = Fc region xELL H435R S354C T366W knob
source                        1..224
                              mol_type = protein
```

```
                     organism = synthetic construct
SEQUENCE: 84
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVMHEALH NRYTQKSLSL SPGK                    224

SEQ ID NO: 85           moltype = AA  length = 224
FEATURE                 Location/Qualifiers
REGION                  1..224
                        note = Fc region xELL M252Y and M428V (YV) S354C T366W knob
source                  1..224
                        mol_type = protein
                        organism = synthetic construct
SEQUENCE: 85
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVVHEALH NHYTQKSLSL SPGK                    224

SEQ ID NO: 86           moltype = AA  length = 224
FEATURE                 Location/Qualifiers
REGION                  1..224
                        note = Fc region xELL M252Y and M428L (YL) S354C T366W knob
source                  1..224
                        mol_type = protein
                        organism = synthetic construct
SEQUENCE: 86
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVLHEALH NHYTQKSLSL SPGK                    224

SEQ ID NO: 87           moltype = AA  length = 224
FEATURE                 Location/Qualifiers
REGION                  1..224
                        note = Fc region xELL M252Y, M428L, H435R (YLR) S354C T366W
                        knob
source                  1..224
                        mol_type = protein
                        organism = synthetic construct
SEQUENCE: 87
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVLHEALH NRYTQKSLSL SPGK                    224

SEQ ID NO: 88           moltype = AA  length = 224
FEATURE                 Location/Qualifiers
REGION                  1..224
                        note = Fc region xELL M252Y, M428V, H435R (YVR) S354C T366W
                        knob
source                  1..224
                        mol_type = protein
                        organism = synthetic construct
SEQUENCE: 88
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVVHEALH NRYTQKSLSL SPGK                    224

SEQ ID NO: 89           moltype = AA  length = 224
FEATURE                 Location/Qualifiers
REGION                  1..224
                        note = Fc region xELL T366S, L368A, Y407V hole
source                  1..224
                        mol_type = protein
                        organism = synthetic construct
SEQUENCE: 89
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NHYTQKSLSL SPGK                    224

SEQ ID NO: 90           moltype = AA  length = 224
FEATURE                 Location/Qualifiers
REGION                  1..224
                        note = Fc region xELL H435R, T366S, L368A, Y407V hole
source                  1..224
```

```
SEQUENCE: 90
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NRYTQKSLSL SPGK                   224

SEQ ID NO: 91            moltype = AA  length = 224
FEATURE                  Location/Qualifiers
REGION                   1..224
                         note = Fc region xELL M252Y and M428V (YV) T366S, L368A,
                         Y407V hole
source                   1..224
                         mol_type = protein
                         organism = synthetic construct
SEQUENCE: 91
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVVHEALH NHYTQKSLSL SPGK                   224

SEQ ID NO: 92            moltype = AA  length = 224
FEATURE                  Location/Qualifiers
REGION                   1..224
                         note = Fc region xELL M252Y and M428L (YL) T366S, L368A,
                         Y407V hole
source                   1..224
                         mol_type = protein
                         organism = synthetic construct
SEQUENCE: 92
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVLHEALH NHYTQKSLSL SPGK                   224

SEQ ID NO: 93            moltype = AA  length = 224
FEATURE                  Location/Qualifiers
REGION                   1..224
                         note = Fc region xELL M252Y, M428L, H435R (YLR) T366S,
                         L368A, Y407V hole
source                   1..224
                         mol_type = protein
                         organism = synthetic construct
SEQUENCE: 93
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVLHEALH NRYTQKSLSL SPGK                   224

SEQ ID NO: 94            moltype = AA  length = 224
FEATURE                  Location/Qualifiers
REGION                   1..224
                         note = Fc region xELL M252Y, M428V, H435R (YVR) T366S,
                         L368A, Y407V hole
source                   1..224
                         mol_type = protein
                         organism = synthetic construct
SEQUENCE: 94
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVVHEALH NRYTQKSLSL SPGK                   224

SEQ ID NO: 95            moltype = AA  length = 227
FEATURE                  Location/Qualifiers
REGION                   1..227
                         note = Fc region H435R
source                   1..227
                         mol_type = protein
                         organism = synthetic construct
SEQUENCE: 95
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNRYTQKS LSLSPGK                227

SEQ ID NO: 96            moltype = AA  length = 227
FEATURE                  Location/Qualifiers
```

```
REGION                          1..227
                                note = Fc region M252Y and M428V (YV)
source                          1..227
                                mol_type = protein
                                organism = synthetic construct
SEQUENCE: 96
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVVHE ALHNHYTQKS LSLSPGK                 227

SEQ ID NO: 97                   moltype = AA  length = 227
FEATURE                         Location/Qualifiers
REGION                          1..227
                                note = Fc region M252Y and M428L (YL)
source                          1..227
                                mol_type = protein
                                organism = synthetic construct
SEQUENCE: 97
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHNHYTQKS LSLSPGK                 227

SEQ ID NO: 98                   moltype = AA  length = 227
FEATURE                         Location/Qualifiers
REGION                          1..227
                                note = Fc region M252Y, M428L, H435R (YLR)
source                          1..227
                                mol_type = protein
                                organism = synthetic construct
SEQUENCE: 98
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHNRYTQKS LSLSPGK                 227

SEQ ID NO: 99                   moltype = AA  length = 227
FEATURE                         Location/Qualifiers
REGION                          1..227
                                note = Fc region M252Y, M428V, H435R (YVR)
source                          1..227
                                mol_type = protein
                                organism = synthetic construct
SEQUENCE: 99
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVVHE ALHNRYTQKS LSLSPGK                 227

SEQ ID NO: 100                  moltype = AA  length = 227
FEATURE                         Location/Qualifiers
REGION                          1..227
                                note = Fc region S354C T366W knob
source                          1..227
                                mol_type = protein
                                organism = synthetic construct
SEQUENCE: 100
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 101                  moltype = AA  length = 227
FEATURE                         Location/Qualifiers
REGION                          1..227
                                note = Fc region H435R S354C T366W knob
source                          1..227
                                mol_type = protein
                                organism = synthetic construct
SEQUENCE: 101
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNRYTQKS LSLSPGK                 227

SEQ ID NO: 102                  moltype = AA  length = 227
FEATURE                         Location/Qualifiers
REGION                          1..227
```

```
                        note = Fc region M252Y and M428L (YL) S354C T366W knob
source                  1..227
                        mol_type = protein
                        organism = synthetic construct
SEQUENCE: 102
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVLHE ALHNHYTQKS LSLSPGK                 227

SEQ ID NO: 103          moltype = AA  length = 227
FEATURE                 Location/Qualifiers
REGION                  1..227
                        note = Fc region M252Y, M428L, H435R (YLR) S354C T366W knob
source                  1..227
                        mol_type = protein
                        organism = synthetic construct
SEQUENCE: 103
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVLHE ALHNRYTQKS LSLSPGK                 227

SEQ ID NO: 104          moltype = AA  length = 227
FEATURE                 Location/Qualifiers
REGION                  1..227
                        note = Fc region M252Y, M428V, H435R (YVR) S354C T366W knob
source                  1..227
                        mol_type = protein
                        organism = synthetic construct
SEQUENCE: 104
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVVHE ALHNRYTQKS LSLSPGK                 227

SEQ ID NO: 105          moltype = AA  length = 227
FEATURE                 Location/Qualifiers
REGION                  1..227
                        note = Fc region T366S, L368A, Y407V hole
source                  1..227
                        mol_type = protein
                        organism = synthetic construct
SEQUENCE: 105
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 106          moltype = AA  length = 227
FEATURE                 Location/Qualifiers
REGION                  1..227
                        note = Fc region H435R, T366S, L368A, Y407V hole
source                  1..227
                        mol_type = protein
                        organism = synthetic construct
SEQUENCE: 106
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRYTQKS LSLSPGK                 227

SEQ ID NO: 107          moltype = AA  length = 227
FEATURE                 Location/Qualifiers
REGION                  1..227
                        note = Fc region M252Y and M428V (YV) T366S, L368A, Y407V
                         hole
source                  1..227
                        mol_type = protein
                        organism = synthetic construct
SEQUENCE: 107
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVVHE ALHNHYTQKS LSLSPGK                 227

SEQ ID NO: 108          moltype = AA  length = 227
FEATURE                 Location/Qualifiers
REGION                  1..227
```

```
                        note = Fc region M252Y and M428L (YL) T366S, L368A, Y407V
                         hole
source                  1..227
                        mol_type = protein
                        organism = synthetic construct
SEQUENCE: 108
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVLHE ALHNHYTQKS LSLSPGK                 227

SEQ ID NO: 109          moltype = AA  length = 227
FEATURE                 Location/Qualifiers
REGION                  1..227
                        note = Fc region M252Y, M428L, H435R (YLR) T366S, L368A,
                         Y407V hole
source                  1..227
                        mol_type = protein
                        organism = synthetic construct
SEQUENCE: 109
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVLHE ALHNRYTQKS LSLSPGK                 227

SEQ ID NO: 110          moltype = AA  length = 242
FEATURE                 Location/Qualifiers
REGION                  1..242
                        note = CD33 ECD
source                  1..242
                        mol_type = protein
                        organism = synthetic construct
SEQUENCE: 110
DPNFWLQVQE SVTVQEGLCV LVPCTFFHPI PYYDKNSPVH GYWFREGAII SRDSPVATNK    60
LDQEVQEETQ GRFRLLGDPS RNNCSLSIVD ARRRDNGSYF FRMERGSTKY SYKSPQLSVH   120
VTDLTHRPKI LIPGTLEPGH SKNLTCSVSW ACEQGTPPIF SWLSAAPTSL GPRTTHSSVL   180
IITPRPQDHG TNLTCQVKFA GAGVTTERTI QLNVTYVPQN PTTGIFPGDG SGKQETRAGV   240
VH                                                                 242

SEQ ID NO: 111          moltype = AA  length = 269
FEATURE                 Location/Qualifiers
REGION                  1..269
                        note = CD33 ECD-AviTagTM-His
source                  1..269
                        mol_type = protein
                        organism = synthetic construct
SEQUENCE: 111
DPNFWLQVQE SVTVQEGLCV LVPCTFFHPI PYYDKNSPVH GYWFREGAII SRDSPVATNK    60
LDQEVQEETQ GRFRLLGDPS RNNCSLSIVD ARRRDNGSYF FRMERGSTKY SYKSPQLSVH   120
VTDLTHRPKI LIPGTLEPGH SKNLTCSVSW ACEQGTPPIF SWLSAAPTSL GPRTTHSSVL   180
IITPRPQDHG TNLTCQVKFA GAGVTTERTI QLNVTYVPQN PTTGIFPGDG SGKQETRAGV   240
VHGGTGGSGL NDIFEAQKIE WHEHHHHHH                                    269

SEQ ID NO: 112          moltype = AA  length = 286
FEATURE                 Location/Qualifiers
REGION                  1..286
                        note = CD33M
source                  1..286
                        mol_type = protein
                        organism = synthetic construct
SEQUENCE: 112
DPNFWLQVQE SVTVQEGLCV LVPCTFFHPI PYYDKNSPVH GYWFREGAII SRDSPVATNK    60
LDQEVQEETQ GRFRLLGDPS RNNCSLSIVD ARRRDNGSYF FRMERGSTKY SYKSPQLSVH   120
VTDLTHRPKI LIPGTLEPGH SKNLTCSVSW ACEQGTPPIF SWLSAAPTSL GPRTTHSSVL   180
IITPRPQDHG TNLTCQVKFA GAGVTTERTI QLNVTYVPQN PTTGIFPGDG SGKQETRAGV   240
VHGAIGGAGV TALLALCLCL IFFIVKTHRR KAARTAVGRN DTHPTT                  286

SEQ ID NO: 113          moltype = AA  length = 120
FEATURE                 Location/Qualifiers
REGION                  1..120
                        note = CD33m
source                  1..120
                        mol_type = protein
                        organism = synthetic construct
SEQUENCE: 113
DLTHRPKILI PGTLEPGHSK NLTCSVSWAC EQGTPPIFSW LSAAPTSLGP RTTHSSVLII    60
TPRPQDHGTN LTCQVKFAGA GVTTERTIQL NVTYVPQNPT TGIFPGDGSG KQETRAGVVH   120

SEQ ID NO: 114          moltype = AA  length = 116
```

| | | |
|---|---|---|
| FEATURE | Location/Qualifiers | |
| REGION | 1..116 | |
| | note = hzA07v4 KP | |
| source | 1..116 | |
| | mol_type = protein | |
| | organism = synthetic construct | |

SEQUENCE: 114
EVQLVESGGG EVQPGGSLRL SCAASRSSGI DVMGWYRQAP GKERELVAEI SGVGDTNYAA  60
SLADRFTVSR DNAKNTVYLQ MSSLRAEDTA VYYCNAHSFL DLVGAWGQGT LVTVKP     116

| | | |
|---|---|---|
| SEQ ID NO: 115 | moltype = AA  length = 124 | |
| FEATURE | Location/Qualifiers | |
| REGION | 1..124 | |
| | note = hzB07v7 KP | |
| source | 1..124 | |
| | mol_type = protein | |
| | organism = synthetic construct | |

SEQUENCE: 115
EVQLVESGGG EVQPGGSLRL SCAASGRTIS DYVVGWFRQA PGKERAFVAA ISRYGTTYYA  60
ASVQGRFTIS RDNPRNTVYL QVDSLRAEDT AVYYCAALQN DVRNNHSPTS YDYWGQGTLV 120
TVKP                                                              124

| | | |
|---|---|---|
| SEQ ID NO: 116 | moltype = AA  length = 120 | |
| FEATURE | Location/Qualifiers | |
| REGION | 1..120 | |
| | note = hz1C7v1 KP | |
| source | 1..120 | |
| | mol_type = protein | |
| | organism = synthetic construct | |

SEQUENCE: 116
EVQLVESGGG EVQPGGSLRL SCAASGRTFS GYIMGWFRQA PGKERELVAR ISGNNLSTEY  60
AESVKGRFTI SRDNAKNTLY LQMSSLRAED TAVYYCAAEY DYSSGDFVYW GQGTLVTVKP 120

| | | |
|---|---|---|
| SEQ ID NO: 117 | moltype = AA  length = 120 | |
| FEATURE | Location/Qualifiers | |
| REGION | 1..120 | |
| | note = hz1C7v11 KP | |
| source | 1..120 | |
| | mol_type = protein | |
| | organism = synthetic construct | |

SEQUENCE: 117
EVQLVESGGG EVQPGGSLRL SCAASGRTFS GYIMGWFRQA PGKERELVAR ISGNNLATEY  60
AESVKGRFTI SRDNAKNTLY LQMSSLRAED TAVYYCAAEY DYSSGDFVYW GQGTLVTVKP 120

| | | |
|---|---|---|
| SEQ ID NO: 118 | moltype = AA  length = 118 | |
| FEATURE | Location/Qualifiers | |
| REGION | 1..118 | |
| | note = hz1E4v2 KP | |
| source | 1..118 | |
| | mol_type = protein | |
| | organism = synthetic construct | |

SEQUENCE: 118
EVQLVESGGG EVQPGGSLRL SCAASGSGFS ASLMSWHRQA PGKQRDLVAS ITRDGRANYV  60
ESVKGRFTIS RDNAKNTLYL QMSSLRAEDT AVYYCHAYSF DYPIRSYWGQ GTLVTVKP   118

| | | |
|---|---|---|
| SEQ ID NO: 119 | moltype = AA  length = 121 | |
| FEATURE | Location/Qualifiers | |
| REGION | 1..121 | |
| | note = hzF02v18 KP | |
| source | 1..121 | |
| | mol_type = protein | |
| | organism = synthetic construct | |

SEQUENCE: 119
EVQLVESGGG EVQPGGSLRL SCAASGSISS YNVMGWYRQA PGKQRELVAQ INAYGDTNYA  60
NAVVGRFTIS RDNAKNTVYL QMSSLRAEDT AVYYCNGQRM LENYTYRDQS WGQGTLVTVK 120
P                                                                 121

| | | |
|---|---|---|
| SEQ ID NO: 120 | moltype = AA  length = 118 | |
| FEATURE | Location/Qualifiers | |
| REGION | 1..118 | |
| | note = hz1G3v3 | |
| source | 1..118 | |
| | mol_type = protein | |
| | organism = synthetic construct | |

SEQUENCE: 120
EVQLVESGGG EVQPGGSLRL SCAASGFTFS SYAMGWFRQA PGKGREWVAA ITTSGDTTYY  60
AESVKGRFTI SRDNAKNTVY LQMSSLRAED TAVYYCAAHR GGGVIDYWGQ GTLVTVKP   118

| | | |
|---|---|---|
| SEQ ID NO: 121 | moltype = AA  length = 120 | |

| FEATURE | Location/Qualifiers |
|---|---|
| REGION | 1..120 |
| | note = hzG11v2 KP |
| source | 1..120 |
| | mol_type = protein |
| | organism = synthetic construct |

SEQUENCE: 121

```
EVQLVESGGG EVQPGGSLRL SCAASGSTLN IDHIGWYRQA PGKERELVGV ISSGAGPNYA    60
ESVKGRFTIS RDNAKNTVYL QMSSLRAEDT AVYYCNAWID YGSGLPQNYW GQGTLVTVKP   120
```

| SEQ ID NO: 122 | moltype = AA  length = 121 |
|---|---|
| FEATURE | Location/Qualifiers |
| REGION | 1..121 |
| | note = hz1H9v2 KP |
| source | 1..121 |
| | mol_type = protein |
| | organism = synthetic construct |

SEQUENCE: 122

```
EVQLVESGGG EVQPGGSLRL SCAASGSIFS ISIMGWYRQA PGKERELVAS TTSSGTTNYV    60
ESVKGRFTIS RDNAKNTLYL QMSSLRAEDT AVYYCHAYIA TTTDRGYRGY WGQGTLVTVK   120
P                                                                  121
```

| SEQ ID NO: 123 | moltype = AA  length = 116 |
|---|---|
| FEATURE | Location/Qualifiers |
| REGION | 1..116 |
| | note = A07 KP |
| source | 1..116 |
| | mol_type = protein |
| | organism = synthetic construct |

SEQUENCE: 123

```
QVQLVQSGGG LVQAGGSLTL SCAASRSSGI DVMGWYRQAP GKERELVAEI SGVGDTNYAA    60
SLADRFTVSR DNAKNTVYLQ MKNLKPEDTA VYYCNAHSFL DLVGAWGQGT QVTVKP       116
```

| SEQ ID NO: 124 | moltype = AA  length = 124 |
|---|---|
| FEATURE | Location/Qualifiers |
| REGION | 1..124 |
| | note = B07 KP |
| source | 1..124 |
| | mol_type = protein |
| | organism = synthetic construct |

SEQUENCE: 124

```
EVQLVQSGGG LVQTGGSLRL SCGASGRTIS DYVVGWFRQA PGKERAFVAA ISRYGTTYYA    60
ASVQGRFTIS RDNPRNTVYL QVDSLRPEDT AVYFCAALQN DVRNNHSPTS YDYWGQGTQV   120
TVKP                                                               124
```

| SEQ ID NO: 125 | moltype = AA  length = 120 |
|---|---|
| FEATURE | Location/Qualifiers |
| REGION | 1..120 |
| | note = 1C7 KP |
| source | 1..120 |
| | mol_type = protein |
| | organism = synthetic construct |

SEQUENCE: 125

```
QVQLQQSGGG LVQAGGSLRL SCAASGRTFS GYIMGWFRQV PGKERELVAR ISGNNLSTEY    60
GGSVKGRFTI SRDSAKETMY LQMNSLKPED TAIYYCAAEY DYSSGDFVYW GQGTQVTVKP   120
```

| SEQ ID NO: 126 | moltype = AA  length = 118 |
|---|---|
| FEATURE | Location/Qualifiers |
| REGION | 1..118 |
| | note = 1E4 KP |
| source | 1..118 |
| | mol_type = protein |
| | organism = synthetic construct |

SEQUENCE: 126

```
QVQLQQSGGG SVQAGGSLRL SCVASGSGFS ASLMSWHRQA PGSQRDLVAS ITRDGRANYV    60
DSVKDRFTIS RDNAKNTAYL QMDSLKPEDT AAYYCHAYSF DYPIRSYWGQ GTQVTVKP    118
```

| SEQ ID NO: 127 | moltype = AA  length = 124 |
|---|---|
| FEATURE | Location/Qualifiers |
| REGION | 1..124 |
| | note = F02 KP |
| source | 1..124 |
| | mol_type = protein |
| | organism = synthetic construct |

SEQUENCE: 127

```
QVQLVQSGGG LVQAGGSLRL SCAASGSISS YNVVGWYRQL SGNERGGRTM VAQINAYGDT    60
NYANAVVGRF TISRDDAKNT VYLHMSNLKP EDTGVYYCNG QRMLENYTYR DQSWGQGTQV   120
TVKP                                                               124
```

```
SEQ ID NO: 128          moltype = AA  length = 118
FEATURE                 Location/Qualifiers
REGION                  1..118
                        note = 1G3 KP
source                  1..118
                        mol_type = protein
                        organism = synthetic construct
SEQUENCE: 128
EVQLQQSGGG EVQPGGSLRL SCEASGFTFS SYAMGWFRQA PGKGREWVAA ITTSGDTTYY    60
AESVKGRFTI SRDNAKNTVY LQMSSLRAED TAVYYCAAHR GGGVIDYWGQ GTQVTVKP    118

SEQ ID NO: 129          moltype = AA  length = 120
FEATURE                 Location/Qualifiers
REGION                  1..120
                        note = G11 KP
source                  1..120
                        mol_type = protein
                        organism = synthetic construct
SEQUENCE: 129
EVQLVQSGGG SVQVGGSLRL SCAASGSTLN IDHIGWYRQA PGKERELVGV ISSGAGPNYA    60
DSVKGRFTIS RDNAKNTVYL QMNSLKPEDT AVYNCNAWID YGSGLPQNYW GQGTQVTVKP  120

SEQ ID NO: 130          moltype = AA  length = 121
FEATURE                 Location/Qualifiers
REGION                  1..121
                        note = 1H9 KP
source                  1..121
                        mol_type = protein
                        organism = synthetic construct
SEQUENCE: 130
EVQLQQSGGA VVQPGGSLRL SCAASGSIFS ISIMGWYRQA PGKERELVAS TTSSGTTNYV    60
DSVKGRFTAS RDNAKNTVYL QMNSLKPDDT AIYHCHAYIA TTTDRGYRGY WGQGTQVTVK  120
P                                                                 121

SEQ ID NO: 131          moltype = AA  length = 117
FEATURE                 Location/Qualifiers
REGION                  1..117
                        note = 401-A9 KP
source                  1..117
                        mol_type = protein
                        organism = synthetic construct
SEQUENCE: 131
QVQLQQSGGG LVQAGGSLRL SCAAPGSINS INVMEWYRQA PGKERDLVAG ITSDGDTNYV    60
DSVPGRFTIT RDNTMRTVDL QMNNLKADDT AVYYCRARDW GSLTDYWGQG TQVTVKP     117
```